US010306883B2

(12) United States Patent
Hilder et al.

(10) Patent No.: US 10,306,883 B2
(45) Date of Patent: Jun. 4, 2019

(54) USE OF POROUS POLYMER MATERIALS FOR STORAGE OF BIOLOGICAL SAMPLES

(71) Applicant: UNIVERSITY OF TASMANIA, Sandy Bay (AU)

(72) Inventors: Emily Frances Hilder, Lenah Valley (AU); Wei Boon Hon, Sandy Bay (AU)

(73) Assignee: University of Tasmania, Sandy Bay (AU)

( * ) Notice: Subject to any disclaimer, the term of this patent is extended or adjusted under 35 U.S.C. 154(b) by 0 days.

(21) Appl. No.: 14/151,689

(22) Filed: Jan. 9, 2014

(65) Prior Publication Data
US 2014/0127669 A1 May 8, 2014

Related U.S. Application Data

(63) Continuation of application No. PCT/AU2012/000826, filed on Jul. 11, 2012.

(51) Int. Cl.
*A01N 1/02* (2006.01)
*C12M 1/00* (2006.01)
*B01J 20/26* (2006.01)
*B01J 20/28* (2006.01)
*B01J 20/32* (2006.01)
*B01L 3/00* (2006.01)

(52) U.S. Cl.
CPC ......... *A01N 1/0278* (2013.01); *A01N 1/0231* (2013.01); *B01J 20/267* (2013.01); *B01J 20/28033* (2013.01); *B01J 20/28042* (2013.01); *B01J 20/28054* (2013.01); *B01J 20/28078* (2013.01); *B01J 20/321* (2013.01); *B01J 20/327* (2013.01); *B01J 20/3272* (2013.01); *B01L 3/508* (2013.01); *C12M 45/22* (2013.01); *B01L 2200/0678* (2013.01); *B01L 2300/069* (2013.01); *B01L 2300/0822* (2013.01)

(58) Field of Classification Search
CPC . A01N 1/0278; A01N 1/0231; B01J 20/3272; B01J 20/28054; B01J 20/28042
See application file for complete search history.

(56) References Cited

U.S. PATENT DOCUMENTS

| 4,514,499 | A | 4/1985 | Noll |
| 4,965,289 | A | 10/1990 | Sherrington et al. |
| 5,130,343 | A | 7/1992 | Frechet et al. |
| 5,306,623 | A * | 4/1994 | Kiser ............. C12Q 1/54 422/417 |
| 5,334,310 | A | 8/1994 | Frechet et al. |
| 5,336,599 | A | 8/1994 | Katajima |
| 5,460,777 | A | 10/1995 | Katajima et al. |
| 5,496,562 | A | 3/1996 | Burgoyne |
| 5,728,457 | A | 3/1998 | Frechet et al. |
| 5,756,126 | A | 5/1998 | Burgoyne |
| 5,929,214 | A | 7/1999 | Peters et al. |
| 5,939,259 | A | 8/1999 | Harvey et al. |
| 5,972,386 | A | 10/1999 | Burgoyne |
| 6,048,457 | A | 4/2000 | Kopaciewicz et al. |
| 6,303,290 | B1 | 10/2001 | Liu et al. |
| 6,693,159 | B1 | 2/2004 | Holmes et al. |
| 6,746,841 | B1 | 6/2004 | Fomovskaia et al. |
| 6,750,059 | B1 | 6/2004 | Blakesley et al. |
| 6,884,345 | B1 | 4/2005 | Irgum et al. |
| 6,887,384 | B1 | 5/2005 | Frechet et al. |
| 7,024,890 | B2 | 4/2006 | Costa et al. |
| 7,151,167 | B2 | 12/2006 | Gjerde et al. |
| 7,431,888 | B2 | 10/2008 | Frechet et al. |
| 7,479,223 | B2 | 1/2009 | DiLeo et al. |
| 7,731,844 | B2 | 6/2010 | Mallet et al. |
| 7,955,594 | B2 | 6/2011 | Greener |
| 9,475,914 | B2 | 10/2016 | Haddad et al. |
| 2003/0033930 | A1 | 2/2003 | Tom et al. |
| 2004/0060864 | A1 | 4/2004 | Shepodd et al. |
| 2004/0138323 | A1 | 7/2004 | Stenzel-Rosebaum et al. |
| 2005/0023456 | A1* | 2/2005 | Frechet ............... H01J 49/0418 250/288 |
| 2005/0032929 | A1 | 2/2005 | Greener |
| 2005/0046086 | A1 | 3/2005 | Lee et al. |
| 2005/0116161 | A1 | 6/2005 | Hafeman et al. |
| 2005/0226916 | A1 | 10/2005 | Cochrum et al. |
| 2006/0021939 | A1 | 2/2006 | Mallet et al. |
| 2006/0042948 | A1 | 3/2006 | Santiago et al. |
| 2006/0094015 | A1 | 5/2006 | Smith et al. |
| 2006/0115384 | A1 | 6/2006 | Wohleb |
| 2006/0131238 | A1 | 6/2006 | Xu |
| 2006/0247361 | A1 | 11/2006 | Shah |
| 2007/0092924 | A1 | 4/2007 | Anderson |
| 2008/0035558 | A1 | 2/2008 | Shah |
| 2008/0081848 | A1 | 4/2008 | Shih et al. |
| 2008/0090295 | A1* | 4/2008 | Feuerstein et al. |
| 2008/0160598 | A1 | 7/2008 | Nozaki et al. |
| 2009/0197341 | A1* | 8/2009 | Patel ................... B32B 27/08 436/63 |
| 2010/0009845 | A1 | 1/2010 | Bonn et al. |
| 2010/0300972 | A1 | 12/2010 | Mallet et al. |
| 2012/0107951 | A1 | 5/2012 | Grenz et al. |
| 2012/0276576 | A1* | 11/2012 | Haddad et al. ............ 435/29 |
| 2013/0164856 | A1 | 6/2013 | Jebrail et al. |

FOREIGN PATENT DOCUMENTS

| EP | 1245401 | 10/2002 |
| WO | WO-99-57599 | 11/1999 |

(Continued)

OTHER PUBLICATIONS

Holdsvendova et al., J Biochem Biophys Methods, 2007, vol. 70, p. 23-29.*

(Continued)

*Primary Examiner* — Kade Ariani
(74) *Attorney, Agent, or Firm* — Wilson Sonsini Goodrich & Rosati

(57) ABSTRACT

The present invention generally relates to the use of porous polymer materials as a medium for the storage of biological samples. The present invention also relates to a method of drying and storage of biological samples on the porous polymer materials. The biological samples include blood and blood plasma samples.

24 Claims, 9 Drawing Sheets

(56) References Cited

FOREIGN PATENT DOCUMENTS

| WO | WO 2000/014505 | 3/2000 |
|---|---|---|
| WO | WO-2005-017487 | 2/2005 |
| WO | WO 2005/102526 | 11/2005 |
| WO | WO-2006-092082 | 9/2006 |
| WO | WO-2006-118887 | 11/2006 |
| WO | WO-2011-082449 | 7/2011 |
| WO | WO-2011-137533 | 11/2011 |
| WO | WO-2013-006904 A1 | 1/2013 |

OTHER PUBLICATIONS

Altun et al., Journal of Chromatography, 2010, vol. 1217, p. 2581-2588.*
Svec et al., Journal of Chromatography A, 2010, vol. 1217, p. 902-924.*
Ferreira et al., Clin. Microbiol. Infect., 2011, vol. 17, p. 1007-1012, published online 2010.*
Li et al., Biomed. Chromatogr., 2010, vol. 24, p. 49-65.*
Abdel-Rehim et al., "Evaluation of monolithic packed 96-tips and liquid chromatography-tandem mass spectrometry for extraction and quantification of pindolol and metroprolol in human plasma samples." Journal of Chromatography A, (2008), pp. 23-27: 1196-1197, Elsevier.
Allanson, et al., "Determination of rifampicin in human plasma and blood spots by high performance liquid chromatography with UV detection: a potential method for therapeutic drug monitoring," Journal of Pharmaceutical and Biomedical Analysis, 2007, 44(4): pp. 963-969.
Bakry et al., "Monolithic porous polymer layer for the separation of peptides and proteins using thin-layer chromatography coupled with MALDI-TOF-MS" Analytical Chemistry, 2007, 79(2): pp. 486-493.
Bisjak et al., "Amino-functionalized monolithic poly(glycidyl methacrylates-co-divinylbenzine) Ion-exchange stationary phases for the separation of oligonucleotides," Chromatographia, 2005, 62 (Supplement 13); S31-36.
Brunauer, et al., "Adsorption of Gases in Multimolecular Layers," Journal of the American Chemical Society, 1938. vol. 60: p. 309-319.
Corso, et al., "Neutral loss analysis of Amino Acids by desorption electrospray ionization using an unmodified tandem quadruple mass spectrometer," Rapid Communications in Mass Spectrometry, 2007. 21: p. 3777-3784.
Davankov et al., "Polymeric adsorbent for removing toxic proteins from blood of patients with kidney failure." Journal of Chromatography B, (2000), pp. 73-80: 739, Elsevier.
Edelbroek, et al., "Dried Blood Spot Methods in Therapeutic Drug Monitoring: Methods, Assays, and Pitfalls." Therapeutic Drug Monitoring, 2009, 31(3): p. 327-336.
Eeltink, et al., "Controlling the surface chemistry and chromatographic properties of methacrylate-ester-based monolithic capillary columns via photografting," J. Sep. Sci., 2007, 30(3), 407-413.
EP11731623 Supplementary EP Search Report dated Jun. 5, 2013.
Gadre et al., "Hybrid Nanomaterial Scaffolds for Specific Biomedical Applications" Mater. Res. Soc. Symp. Proc. vol. 1237 (2010).
Hambidge, Michael, "Biomarkers of Nutritional Exposure and Nutritional Status: Biomarkers of Trace Mineral Intake and Status," Journal of Nutrition, 2003. 133(3): p. 9485-9555.
Nordberg, et al., "Recent advances in polymer monoliths for ion-exchange chromatography," Analytical and Bioanalytical Chemistry, 2009, 394(1): pp. 71-84.
PCT/AU2011/000008 International Preliminary Report on Patentability dated Nov. 15, 2011.
PCT/AU2011/000008 International Search Report dated Feb. 4, 2011.
PCT/AU2012/000826 International Search Report dated Aug. 13, 2012.
PCT/AU2012/000826 International Preliminary Report on Patentability dated Jan. 23, 2014.
Potter, et al., "Porous Polymer monoliths for extraction: Diverse applications and platforms," J. Sep. Sci., 2008, 31, pp. 1881-1906.
Qu et al., "Preparation and Characterization of Large Porous Poly (HEMA-co-EDMA) Microspheres with Narrow Size Distribution by Modified Membrane Emulsification Method." Journal of Applied Polymer Science (2007) pp. 1632-1641: 105.
Rober et al., "New 3-D microarray platform based on macroporous polymer monoliths." Analytica Chimica Acta 644 (2009): 95-103, Elsevier.
Saunders, et al., "Separation and sample pre-treatment in bioanalysis using monolithic phases: A review." Analytica Chimica Acta 652 (2009): 22-31 Elsevier.
Svec, et al., "Kinetic Control of Pore Formation in Macroporous polymers. Formation of "Molded" Porous Materials with High Flow Characteristics for Separations or Catalysis," 1995, 7(4): pp. 707-715.
Thabano et al., "Selective extraction and elution of weak bases by in-line solid-phase extraction capillary electrophoresis using a pH step gradient and a weal-cation-exchange monolith," The Analyst, 2008, 133(10), 1380-1387.
U.S. Appl. No. 13/520,546 Office Action dated Oct. 1, 2013.
Ueki et al., "Preparation and application of methacrylate-based cation-exchange monolithic columns for capillary ion chromatography," Analytical Chemistry, 2004, 76(23): pp. 7007-7012.
Uyama, Y. et al., "Surface Modification of Polymers by Grafting" Adv. Polym. Sci. 1998, vol. 137, pp. 1-39.
Uzen et al., "Poly(ethylene dimethacrylate-glycidyl methacrylate) Monolith as a Stationary Phase in Dye-Affinity Chromatography" Ind. Eng. Chem. Res., 43:6507-6513 (2004).
Viklund, C. et al. "Synthesis of Porous Zwitterionic Sulfobetaine Monoliths and Characterization of Their Interaction with Proteins" Macromolecules 2000, vol. 33, No. 7, pp. 2539-2544.
Xie, et al., "Porous Polymer Monoliths: Preparation of Sorbent Materials with High-Surface Areas and Controlled Surface Chemistry for High-Throughput, Online, Solid-Phase, Extraction of Polar Organic Compounds," 1998 Chem. Mater., vol. 10, No. 12, pp. 4072-4078.
Yu, et al, "Preparation of Monolithic Polymers with Controlled Porous Properties for Microfluidic Chip Applications Using Photoinitiated Free-Radical Polymerization," Journal of Polymer Science: Part A: Polymer Chemistry, 2002, vol. 40, pp. 755-769.
EP12811104.4 Supplementary EP Search Report dated Jan. 28, 2015.
U.S. Appl. No. 13/520,546 Office Action dated Jul. 17, 2014.

* cited by examiner

USE OF POROUS POLYMER MATERIALS FOR STORAGE OF BIOLOGICAL SAMPLES

CROSS-REFERENCE

This application is a continuation application of International Application No. PCT/AU2012/000826, filed Jul. 11, 2012, which claims the benefit of Australian Patent Application No. 2011902782, filed Jul. 12, 2011, each of which is incorporated herein by reference in its entirety.

FIELD

The present invention generally relates to the use of porous polymer materials as a medium for the storage of biological samples. The present invention also relates to a method of drying and storage of biological samples on the porous polymer materials. The biological samples include blood and blood plasma samples.

BACKGROUND

The sampling technique known as dried blood spotting (DBS) was developed by the microbiologist Robert Guthrie in 1963. The sample collection procedure is simplistic, involving the collection of a very small volume of blood from a small incision to the heel or finger. A drop of blood is then directly applied to a sampling paper and dried for future analyte extraction. DBS sampling is now a common and established practice for the quantitative and qualitative screening of metabolic disorders in newborns (Edelbroek, P. M., J. van der Heij den, and L. M. L. Stolk, *Dried Blood Spot Methods in Therapeutic Drug Monitoring: Methods, Assays, and Pitfalls*. Therapeutic Drug Monitoring, 2009. 31(3): p. 327-336).

Conventional sampling techniques employ plasma or serum as the biological matrix of choice for analysis. These techniques require large volumes of blood to be collected directly from the vein of a test subject. Conversely, DBS sampling requires substantially smaller sample volumes (microliters as opposed to milliliters) which allows sample collection in situations where collection in the traditional manner may be difficult and is now routinely applied to epidemiological studies, and for example has been successfully implemented for assaying numerous biological markers such as amino acids (Corso, G., et al., *Rapid Communications in Mass Spectrometry*, 2007. 21(23): p. 3777-3784), and trace elements (Hambidge, M., Journal of Nutrition, 2003. 133(3): p 9485-9555).

DBS methodologies are particularly suitable for the analysis of infectious agents such as HIV and HCV, as the reduced sample volumes minimize the risk of infection and blood is no longer considered to be a biohazard once dried, which drastically simplifies the storage and transportation of samples (Allanson, A. L., et al., Journal of Pharmaceutical and Biomedical Analysis, 2007, 44(4): p 963-969). Without specialised storage requirements samples can be easily and cost effectively transported around the world. The technique affords a further advantage in that equipment such as centrifuges and freezers are not required for sample processing or storage.

DBS technologies have also been applied in pharmacokinetic analysis to analyse components in blood.

The medium currently used in DBS methodologies, which involves the drying and storage of blood and plasma samples prior to future extraction and analysis, comprises paper based cellulose materials. For example, modified paper based materials have been developed for simplified isolation of nucleic acid; where the paper is chemically treated with a range of compounds to promote the long term storage of DNA. However, paper based cellulose materials are not particularly suited to accelerated drying procedures, particularly with blood plasma, and are not suited to incorporating specific functionalities to facilitate selective extraction of components from blood.

There is consequently a need to identify alternative materials that provide properties for facilitating the drying and storage of biological samples including body fluids such as blood and plasma samples, for future extraction and analysis, or to allow specific functionality to be incorporated into the storage medium.

SUMMARY

In a first aspect, there is provided a use of a porous polymer material as a medium for drying and storage of a biological fluid sample, wherein the porous polymer material is selected from a porous polymer matrix material or a porous polymer monolith material, wherein the porous polymer monolith material is formed by a step-growth polymerisation process.

The biological fluid sample may be a body fluid selected from blood, urine, mucous, synovial fluid, cerebrospinal fluid, tears, or other bodily secretion. In an embodiment, the use of the porous polymer material as a medium is for the storage of whole blood. In a preferred embodiment, the use is for dried blood spotting (DBS). In another embodiment, the use of the porous polymer material as a medium is for the storage of blood plasma. In a preferred embodiment, the use is for dried blood plasma spotting (DPS).

In an embodiment, there is provided a use of a porous polymer matrix material as a medium for drying and storage of a biological fluid sample. In another embodiment, there is provided a use of a porous polymer monolith material as a medium for drying and storage of a biological fluid sample.

The porous polymer material medium has an integral body with a pore size and/or specific surface area adapted to facilitate the drying and storage of body fluids.

In an embodiment, the pore size of the porous polymer material is in the range of 5 to 10,000 nm, 50 to 5,000 nm, 100 to 2,000 nm, 200 to 1000 nm. A smaller pore size correlates to a higher surface area that facilitates the adsorption of biological fluids such as blood and blood plasma. In another embodiment, the specific surface area of the porous polymer material when measured by nitrogen adsorption using BET isotherm is in the range of 0.5 to 1000 m2/g, 1 to 500 m2/g, 5 to 200 $m^2/g$, 10 to 100 $m^2/g$, 20 to 60 $m^2/g$, 30-50 $m^2/g$.

The porous polymer material medium as described above is capable of receiving a biological fluid sample in liquid form and subsequently being dried to facilitate storage, transport and/or future analysis of the sample. The porous polymer material medium can be adapted to facilitate the adsorption or adherence of a body fluid, such as blood and blood plasma. In a particular embodiment, the medium is adapted for storing blood and/or blood plasma. For example, the porous polymer material may be provided with chemical functionality such as hydrophilic groups. The chemical functionality may be incorporated into the polymer materials on polymerisation thereof. The chemical functionality may be incorporated after polymerisation, such as during the preparation of the medium or functionalisation after the medium has been prepared. The chemical functionality may involve covalent bonding of functional groups into the polymer chains. The chemical functionality may be adapted to facilitate pre-analysis or in situ purification of the biological sample on the medium, such as extraction of one or more particular components in the sample.

In another embodiment, functionality can be incorporated into the porous polymer material for in situ elimination of undesirable components in blood that impede the detection of other particular components, for example analytes such as pharmaceutical agents or new chemical entities (NCE). In one particular embodiment, at least the surface of the porous polymer material is modified to provide ion exchange properties to facilitate post-storage analysis of any analytes present in the sample. In another particular embodiment, the surface area of the porous polymer material can be provided with ion exchange properties to facilitate the adherence thereon of selected pharmaceutical agents or non-adherence of selected contaminants present in the body fluid. The porous polymer material may therefore be used to analyse body fluids dried thereon without the need for chemical based pre-treatment. In another particular embodiment, the ion exchange properties may be provided by functional groups present on a monomer from which the porous polymer material is formed, and/or a post polymerisation surface modification comprising post-polymerisation grafting or other chemical modification. In a preferred embodiment, the post polymerisation surface modification is photografting.

In an embodiment, there is provided a use of a porous polymer matrix material as a medium for drying and storage of a biological fluid sample.

In an embodiment, the porous polymer matrix material is selected from at least one of a polyolefin, polyether, polyester, polyamide, polycarbonate, polyurethane, polyanhydride, polythiophene, polyvinyl and epoxy resins, preferably at least one polyolefin, polyester or polyamide. Suitable polyolefins include polyethylene, polypropylene and polystyrene.

The porous polymer matrix material may be optionally functionalised with a group selected from at least one of hydroxyl, alkyl, sulphonyl, phosphonyl, carboxyl, amino, nitro, acrylates and methacrylates.

The porous polymer matrix material may be a porous polymer particle material or a porous polymer fibre material. The porous polymer matrix material may be provided in various forms selected from or comprising a foam, sponge, woven or non-woven fabric, agglomerated particle or fibre based material, or composite material thereof. The porous polymer matrix material may provide an open cell interconnected network structure.

In an embodiment, the porous polymer matrix material is a porous polymer particle material formed by sintering an agglomeration of polymer particles optionally with one or more additives. In an embodiment, the polymer particles are selected from at least one of polyester; polyethylene including high density polyethylene, polyethylene tetraphthalate, polyvinylidene fluoride (PVDF) and polytetrafluoroethylene (PTFE); and polypropylene such as high density polypropylene.

In an embodiment, the porous polymer matrix material is a porous polymer fibre material comprising an agglomeration of polymer fibres optionally with one or more additives. In an embodiment, the polymer fibre is selected from at least one of polyester; polyethylene including polyethylene tetraphthalate, polyvinylidene fluoride (PVDF) and polytetrafluoroethylene (PTFE); and polypropylene such as high density polypropylene.

In an embodiment, there is provided a use of a porous polymer monolith material as a medium for drying and storage of a biological fluid sample, wherein the porous polymer monolith material is formed by a step-growth polymerisation process.

The step growth polymerisation process may comprise the polymerisation of one or more monomers having functional groups selected from one or more of hydroxyl, carboxylic acid, anhydride, acyl halide, alkyl halide, acid anhydride, acrylate, methacrylate, aldehyde, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, or azide functional groups. The monomers may have functional groups selected from one or more of hydroxyl, ester, amine, aldehyde, and carboxylic acid.

In one embodiment, the monomer is an acrylic acid monomer such as a methacrylate monomer, for example hydroxyethyl methacrylate (HEMA) and ethylene glycol dimethacrylate (EDMA).

In one embodiment, the porous polymer monolith material can be prepared by polymerising a polymerisation mixture comprising one or more monomers in the presence of a crosslinking monomer, an initiator, and a porogen. The polymerisation mixture may be disposed on and/or in a support material which may include the porous polymer matrix material described herein and polymerisation can be initiated thereon so as to form a porous polymer monolith, which can then be washed with a suitable solvent to remove the porogen. The polymerisation mixture can also be prepared and polymerized first and then disposed upon the support material.

The porous polymer monolith material may be obtained from a polymerisation mixture comprising a monomer in a range of 10-90 vol %, more typically 20-80 vol %, a porogen in a range of 10-90 vol %, more typically 20-80 vol %, and an initiator in a range of 0.5-5 vol %, more typically about 1 vol %.

In a second aspect, there is provided a method of storing a body fluid for future analysis comprising applying a biological fluid sample to the porous polymer material as described herein and drying the biological fluid sample such that the sample at least partially solidifies and adsorbs or adheres to the porous polymer material.

In a third aspect, there is provided a method of storing a body fluid for future analysis comprising:

applying one or more biological fluid samples to one or more regions of the porous polymer material medium as described herein;

partially drying the one or more samples applied to the medium;

optionally separating any one or more regions of the medium having sample applied thereto from regions without sample applied thereto;

optionally further drying the one or more samples applied to the one or more regions of the medium; and storing the one or more samples applied to the one or more regions of the medium.

In an embodiment, the method comprises the step of separating any one or more regions of the medium having sample applied thereto from regions without sample applied thereto. In a further embodiment, the method comprises the step of further drying the one or more samples applied to the one or more regions of the medium before storing the one or more samples applied to the one or more regions of the medium.

In an embodiment, the separating of any one or more regions of the porous polymer material medium having sample applied thereto from regions without sample applied thereto, may comprise substantially removing any medium not having body fluid applied thereto from around the sample, for example trimming or cutting away medium at or near the perimeter of the sample. The medium may be trimmed or cut away from around the sample such that the sample substantially covers the surface of the region to which the sample was applied. In one particular embodiment, a hole-punch is used to separate and obtain the one or more regions of the porous polymer material medium having sample applied thereto.

The method may further comprise the identification and detection of an analyte from the stored sample applied to the medium. In an embodiment, the stored body fluid sample can be analysed without pre-treatment and/or removal from the porous polymer material medium. In another embodiment, the method can comprise pre-treating the sample stored on the medium before analysing the sample thereof.

In an embodiment, the drying of the biological fluid sample, such as blood or blood plasma, is enhanced by application of at least one of elevated temperature, forced convection or reduced pressure. The elevated temperature may be in a temperature range above ambient but below the temperature at which the integrity of storage medium or sample is compromised. In a particular embodiment the elevated temperature is in the range between 30 and 150° C., 40 and 120° C., and more particularly between about 60 and 100° C., or at 30° C. and above, 50° C. and above, 70° C. and above, 90° C. and above, 110° C. and above, or 130° C. and above. In a particular embodiment the elevated temperature is above about 90° C. In another particular embodiment, the reduced pressure is in the range of 5 to 760 mmHg.

In a fourth aspect, there is provided a method of analysis involving the identification and detection of an analyte from a stored biological fluid sample adsorbed or adhered to the porous polymer material medium as described herein.

In an embodiment, the stored biological fluid sample is analysed without pre-treatment and/or removal from the porous polymer material medium. The analysis is typically for analytes. The analytes can include small molecules and low molecular weight compounds present in blood or blood plasma samples, for example, pharmaceutical agents including new chemical entities (NCEs) and any metabolites thereof, peptides, proteins, oligonucleotides, oligosaccharides, lipids or other labile compounds. In another embodiment, the analysis involves the simultaneous analysis of at least two analytes. In a particular embodiment, the at least two analytes comprise an NCE and a metabolite thereof.

In an fifth aspect, there is provided a method for storing and subsequent analysis of a biological fluid sample comprising genetic material, the method comprising:
applying a biological fluid sample comprising one or more analytes to the porous polymer material medium as described herein;
drying the sample applied to the medium;
storing the sample;
retrieving the sample;
optionally pre-treating the sample; and
analysing the sample for the one or more analytes.

DETAILED DESCRIPTION OF THE DRAWINGS

Figure 7:
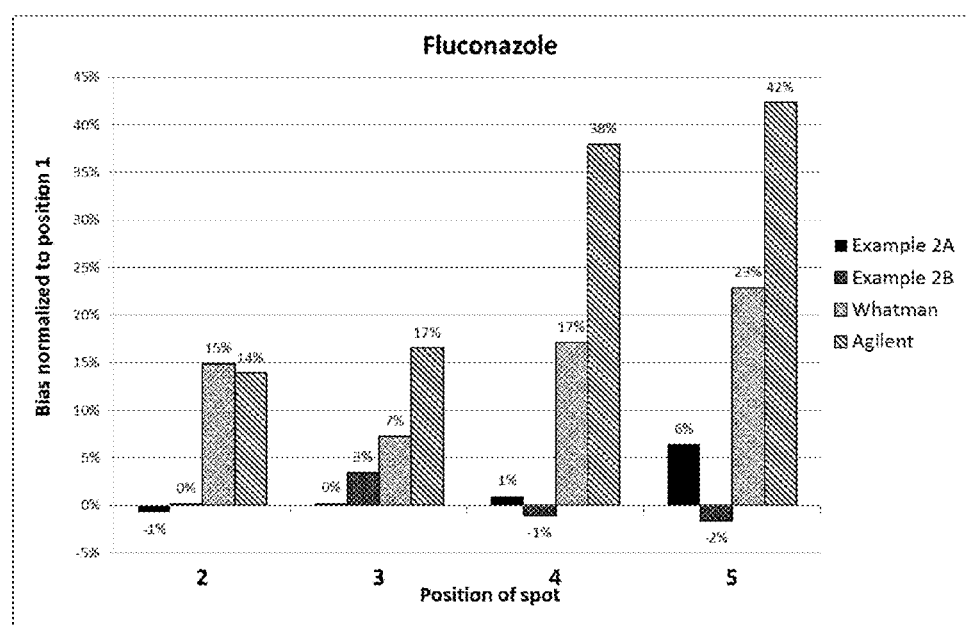
Figure 8:
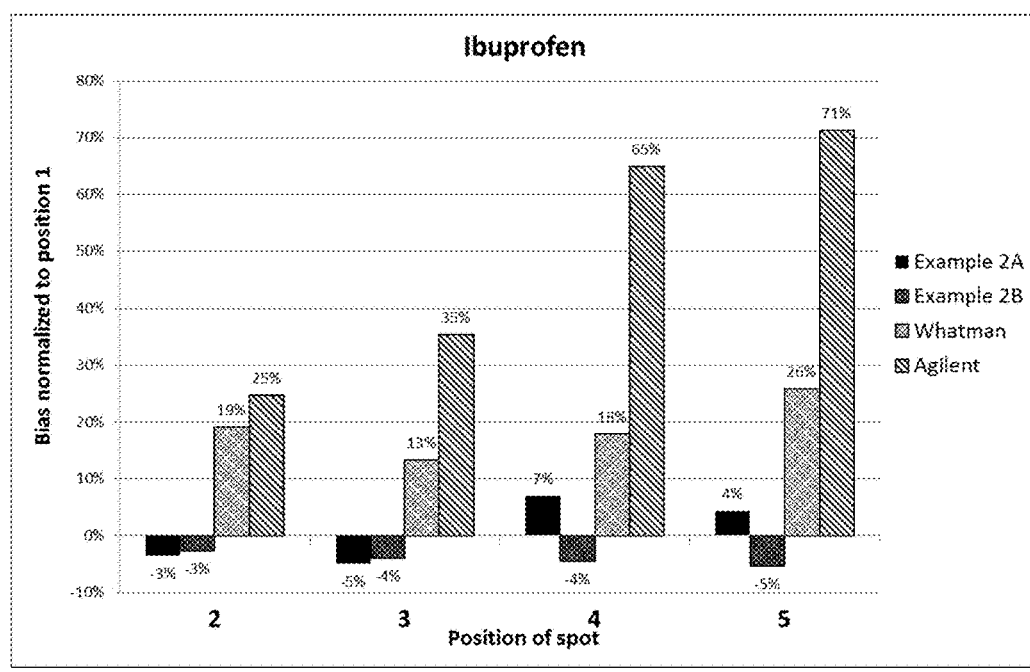

FIG. 7 is a graph showing the consistency of the recovery of Fluconazole from different positions (2, 3, 4 and 5) within the dried blood spots normalized to position 1; and FIG. 8 is a graph showing the consistency of the recovery of Ibuprofen from different positions (2, 3, 4 and 5) within the dried blood spots normalized to position 1.

Figure 9:
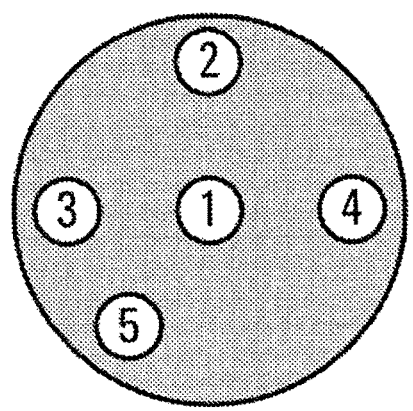

FIG. 9 shows the relative locations of the blood spot punches described in Examples 2A and 2B.

DETAILED DESCRIPTION OF THE ABBREVIATIONS

In the Examples, reference will be made to the following abbreviations in which:
AFM Atomic Force Microscopy
APP Applications
C Celsius
Cl Class
[ ] Concentration
EMAA polyethylene methacrylic acid
F Fahrenheit
FTIR Fourier Transform Infrared
h Hour
HDPE High-density polyethylene
Mn Number average molecular weight
Mw Weight average molecular weight
MW Molecular weight
RH Relative Humidity
SEM Scanning Electron Microscopy
SENB Single edge notched bar
TDCB Tapered double cantilever beam
TETA Triethyltetramine
Wt % Weight percentage of specific component in composition
XPS X-Ray Photoelectron Spectroscopy
DEGDMA Diethylene glycol dimethacrylate
DMPAP 2,2-dimethoxy-2-phenyl-acetophenone
EDMA Ethylene glycol dimethacrylate
GMA Glycidyl methacrylate
HEMA 2-hydroxyl ethyl methacrylate
MAA Methacrylic acid
γ-MAPS 3-(trimethoxysilyl) propyl methacrylate
META Methacryloyloxyethyl trimethylammonium chloride
SPMA 3-sulfopropyl methacrylate
UHMWPE Ultra-high molecular weight polyethylene
RE Relative area
CV Coefficient of variation

DETAILED DESCRIPTION

In an attempt to identify alternative materials that provide properties for facilitating the drying and storage of biological fluid samples for future extraction and analysis, such as blood and plasma samples, and to identify materials that may allow specific functionality to be incorporated therein, it has now been found that a biological fluid sample storage medium can be formed from a range of porous polymer materials. The non-limiting particular embodiments of the present invention are described as follows.

The present invention generally relates to the use of a porous polymer material as a medium for storing a dried biological fluid, particularly blood and blood plasma. The porous polymer materials described herein can therefore provide an appropriate medium for use in DBS methodologies, as an alternative to the paper based cellulose materials currently being used. In particular embodiments the porous polymer materials provide an improved medium for use in storing biological matter for later analytical examination, such as storage of blood and plasma samples for future detection and identification of analytes including small molecules, such as pharmaceutical agents and associated metabolites, and low molecular weight compounds such as proteins and oligonucleotides. The porous polymer materials have excellent properties that have been identified to enable the efficient drying and long term storage of biological fluid samples including blood and blood plasma.

A further advantage of employing the porous polymer materials as a sorbent for DBS is that these materials allow a degree of control over the morphology and surface chemistry of the materials.

Typically, the porous polymer materials are synthetic polymers with a high degree of crosslinking. For example, the porous polymer materials are not cellulose or paper based materials.

Terms

A "porous polymer matrix material" generally refers to a continuous porous polymer matrix having an integral body wherein porosity of the material is formed in a post-polymerisation process.

A "porous polymer particle material" generally refers to a continuous porous polymer matrix having an integral body comprising an agglomeration of polymer particles wherein porosity of the material is formed in a post-polymerisation process.

A "porous polymer fibre material" generally refers to a continuous porous polymer matrix having an integral body comprising an agglomeration of polymer fibres wherein porosity of the material is formed in a post-polymerisation process.

A "porous polymer monolith material" generally refers to a continuous porous polymer matrix having an integral body comprising a fused array of microglobules separated by pores wherein porosity of the material is formed in an in situ polymerisation process.

"Step-growth polymerisation" refers to a type of polymerisation mechanism in which bi-functional or multi-functional monomers react to form polymer chains and crosslinked networks.

A "biological fluid sample" or "body fluid" refers to any fluid that can be taken as a sample from the body of an organism and which may contain a detectable analyte or genetic material, for example blood or blood plasma from a human or animal subject.

An "analyte" includes but is not limited to small molecules and low molecular weight compounds that may be detected in a body fluid, such as a pharmaceutical agent present in a blood or blood plasma sample obtained from a human or animal subject. For example, an "analyte" may include pharmaceutical agents including NCEs, peptides, proteins, oligonucleotides, oligosaccharides, lipids or other labile compounds.

The term "medium" when used in association with another term, such as a "porous polymer material medium" generally refers to the material by itself or further associated with a support material, such as one or more additional layers including a backing layer or protective layer. The medium can provide a stationary support for a biological fluid sample.

A "support material" or like term is a supporting layer or structure that may be associated with the polymer monolith by attachment, removable attachment, or non-attachment, for example, the polymer material may be polymerised on the support material or may merely sit upon the support material with or without other intervening layers that may also be associated with the polymer material and support material by way of attachment, removable attachment or non-attachment. The support material may be flexible, semi-rigid or rigid and may be in any desired form, such as a film or membrane, and may be formed from any appropriate material including glass, polymers, metals, ceramics, or combination thereof.

The term "alkyl" means any saturated or unsaturated, branched or unbranched, cyclised, or combination thereof, typically having 1-10 carbon atoms, which includes methyl, ethyl, propyl, isopropyl, butyl, isobutyl, t-butyl, pentyl, cyclopentyl, isopentyl, neopentyl, hexyl, isohexyl, cyclohexyl, which may be optionally substituted with methyl.

The term "alkylene" means any branched or unbranched, cyclised, or combination thereof, typically having 1-10 carbon atoms, which includes methyl, ethyl, propyl, isopropyl, butyl, isobutyl, t-butyl, pentyl, cyclopentyl, isopentyl, neopentyl, hexyl, isohexyl, cyclohexyl, which may be optionally substituted with methyl.

The term "polymer" includes copolymers, and the term "monomer" includes co-monomers.

The term "porogen", "porogenic solvent" or like term, refers to a solvent capable of forming pores in a polymer matrix during polymerisation thereof, and includes but is not limited to aliphatic hydrocarbons, aromatic hydrocarbons, esters, amides, alcohols, ketones, ethers, solutions of soluble polymers, and mixtures thereof.

The term "initiator" refers to any free radical generator capable of initiating polymerisation by way of thermal initiation, photoinitiation, or redox initiation.

Porous Polymer Matrix Material

The porous polymer matrix material comprises a continuous porous polymer matrix having an integral body wherein porosity of the material is formed in a post-polymerisation process.

The porous polymer matrix material may be a porous polymer particle material or a porous polymer fibre material.

The porous polymer matrix material can be provided in range of sizes, configurations, shapes, or forms, depending on the particular intended use. The material may be formed from a process selected from at least one of sintering, extrusion, emulsion, interfacial polymerisation, and woven fibre preparation.

The porous polymer matrix material involves a post-polymerisation process to introduce porosity. For example, a polymer material, which may include functionality and comprise one or more additives, is first prepared. The prepared polymer material can then be machined or processed (e.g. milled, ground or extruded) into sized extrusions, units, strips, fibres or particles, to facilitate handling and incorporation of additional components or materials.

The extrusions, units, strips, fibres or particles, in addition to other additives, can then be combined or agglomerated together such as by sintering into a solid material to form a medium containing a particular porosity. The medium or material may be processed to introduce porosity (e.g. by washing and removal of an additive present in the polymer material).

In an embodiment, the porous polymer matrix material is selected from at least one of a polyolefin, polyether, polyester, polyamide, polycarbonate, polyurethane, polyanhydride, polythiophene, polyvinyl and epoxy resins, preferably at least one polyolefin, polyester or polyamide.

Suitable polyolefins include polyethylene, polypropylene and polystyrene. The polyethylene (co)polymer may be selected from at least one of ultra-high molecular weight polyethylene, high-density polyethylene, polytetrafluoroethylene, ethylene vinyl acetate, ethylene methyl acrylate, ethylene-propylene rubbers, ethylene-propylene-diene rubbers, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinylidene chloride), poly(tetrafluoroethylene) (PTFE), poly(vinylidene fluoride) (PVDF), polyacrylate, polymethacrylate, PET or PTFE, or a mixture thereof. The polystyrene may be acrylonitrile-butadiene-styrene (ABS). The polyether may be selected from at least one of an ether ketone (PEEK), (poly(oxy-1,4-phenylene-oxy-1,4-phenylene-carbonyl-1,4-phenylene)), and polyether sulfone (PES). The polyamide may be selected from a nylon such as nylon-6.

The porous polymer matrix material may be optionally functionalised with a group selected from at least one of hydroxyl, alkyl, sulphonyl, phosphonyl, carboxyl, amino, nitro, acrylates and methacrylates.

It will be understood that the porous nature of the polymer matrix material provides one or more channels through which gas or liquid molecules can pass. The average pore size may be in the range of about 0.1 µm to 1000 µm. A particularly suitable average pore size may be in a range of about 1 µm to about 500 µm, for example in a range of 1-150 µm, 5-100 µm, or 10-50 µm. It will be appreciated that mean pore size and pore density can be readily determined using a mercury porosimeter or scanning electron microscopy.

A variety of methods known to those skilled in the art can be used to make a porous medium of a polymer material, for example by sintering, using blowing agents and/or leaching agents, microcell formation methods, drilling, reverse phase precipitation or hydroentanglement. The porous material may contain regular arrangements of channels of random or well-defined diameters and/or randomly situated pores of varying shapes and sizes. Pore sizes are typically referred to in terms of average diameters, even though the pores themselves are not necessarily spherical.

In an embodiment, the porous polymer particle material can be formed by sintering of polymer particles, optionally with one or more additives.

The particular method used to form the pores or channels of a porous polymer material and the resulting porosity (i.e., average pore size and pore density) can vary according to the desired application. The desired porosity can be affected by the porous polymer material can alter the physical properties (e.g., tensile strength and durability) of the materials.

The relative amounts of polymer and optionally the additive used to provide a porous polymer material will vary with the specific materials used, the desired functionality of the material surface, and the strength and flexibility of the material itself.

The polymer, functional additive, or optional additional materials, which may be in the form of particles, can be blended to provide a uniform mixture, which can then be sintered. Depending on the desired size and shape of the final product (e.g., a block, tube, cone, cylinder, sheet, or membrane), this can be accomplished using a mould, a belt line, or other techniques known to those skilled in the art. Suitable moulds are commercially available and are well known to those skilled in the art. Specific examples of moulds include, but are not limited to, flat sheets and round cylinders of varying heights and diameters. Suitable mould materials include, but are not limited to, metals and alloys such as aluminium and stainless steel, high temperature thermoplastics, and other materials both known in the art and disclosed herein.

In an embodiment, a compression mould is used to provide the sintered material. The mould is heated to the sintering temperature of the polymer, allowed to equilibrate, and then subjected to pressure. This pressure typically ranges between about 1 psi to about 10 psi, depending on the composition of the mixture being sintered and the desired porosity of the final product. In general, the greater the pressure applied to the mold, the smaller the average pore size and the greater the mechanical strength of the final product. The duration of time during which the pressure is applied also varies depending on the desired porosity of the final product, and is typically about 2 to about 10 minutes.

Once the porous material has been formed, the mould is allowed to cool. If pressure has been applied to the mould, the cooling can occur while it is still being applied or after it has been removed. The material is then removed from the mould and optionally processed. Examples of optional processing include, but are not limited to, sterilizing, cutting, milling, polishing, encapsulating, and coating.

A variety of materials of varying sizes and shapes can be used to provide a suitable porous material. A narrow particle size distribution allows the production of a material with uniform porosity (i.e., a substrate comprising pores that are evenly distributed throughout it and/or are of about the same size), which allows solutions and gases to flow more evenly through the material and provides materials with fewer structural weak spots.

The porous polymer fibre material is a continuous porous polymer matrix with a particular pore size range having an integral body formed from polymer fibres. The general process of producing the porous polymer fibre material involves the initial formation of polymer fibres, which in a subsequent step are brought together to form the porous polymer fibre material. The pore characteristics of the porous polymer fibre material are not determined during the initial polymerisation process, but in the process of bringing the previously produced fibres together when forming the material or during re-forming or post-formation modification of the material.

The polymer fibres may be agglomerated to form an interconnected porous polymer network. The interconnected porous polymer network may be of an open cell type. The polymer fibres may be oriented or randomly agglomerated. The polymer fibres may be woven or non-woven. The porous polymer fibre material may comprise one or more types of continuous polymer fibres. The porous polymer fibre material may comprise one or more types of non-continuous fibres, such as cut or blended fibres. The fibers can be composed of a core and an outer sheath. Different types of fibres may be blended together. The porous polymer fibre material may comprise a fibrous structure. Rigid open-cell structures may be formed. The material may be provided in different shapes and sizes, which can include sheets, tubes, rods, or other three-dimensional geometrical shapes.

The polymer fibres of the porous polymer fibre material may be selected from at least one of polyester; polyethylene including polyethylene tetraphthalate, polyvinylidene fluoride (PVDF) and polytetrafluoroethylene (PTFE); and polypropylene such as high density polypropylene. The polymer fibres or the material can be further modified to increase hydrophilicity. The polymers may be blended or different types of polymer fibres combined.

Various structural fibers may be added to the material to provide strength and rigidity.

A particularly suitable pore size range of the polymer material may be about 10 to about 250 µm. A particularly suitable pore volume range may be 25% to 95%. A density range for the porous polymer fibre material may be, for example, from 12 g/cubic cm to 0.6 g/cubic cm.

Porous Polymer Monolith Materials

Porous polymer monoliths are typically highly cross-linked structures that can function as a stationary support. The internal structure of porous polymer monolith materials consists of a fused array of microglobules that are separated by pores and their structural rigidity is secured by extensive crosslinking. The porosity of the monolith material is formed in an in situ polymerisation process in forming the monolith material.

Porous polymer monolith materials can be fabricated from a mixture containing an initiator and monomers (including crosslinking monomers) dissolved in the pore-forming solvents known as porogens. Formation of the monolith is triggered by a breakdown of the initiator by an external source (e.g. photoinitiation) creating a radical which induces the formation of polymer chains that precipitate out of the polymerisation mixture eventually agglomerating together to form a continuous solid structure. The morphology of the monolith can be controlled by numerous variables; the crosslinking monomer(s) employed, the composition and percentage of the porogenic solvents (porogens), the concentration of the free-radical initiator and the method used to initiate polymerisation.

As polymer monoliths are typically continuous rigid structures, they can be readily fabricated in situ in a range of formats, shapes or sizes. Monoliths have been typically fabricated within the confines of chromatographic columns or capillaries for numerous chromatographic applications. However, given an appropriate mould it is also possible to fabricate monoliths in the format of flat sheets. Flat monolithic sheets provide a particularly suitable medium for the storage of whole blood which allows for ease in both storage and transportation of blood samples.

A further advantage of using porous polymer monolith materials for DBS stems from the ability to be able to control both the porous properties and the specific surface chemistries. The ability to incorporate specific functionality to the monolith surface allows for the specific extraction of analytes, for example pharmaceutical agents or new chemical entities (NCE), as well as facilitating matrix elimination that may degrade future analysis. Future analysis may include solid phase extraction (SPE), which is based on physisorption of analytes on a suitable medium and thus to obtain maximum analyte recovery the medium should possess a large surface area. The porous properties of the medium can also be used to control the specific surface chemistry to a degree as the surface area and thus the ion-exchange capacity of the medium is dependent on the porous properties. The detection and identification of analytes may include small molecules and low molecular weight compounds present in the blood or blood plasma samples, for example, pharmaceutical agents including NCEs, peptides, proteins, oligonucleotides, oligosaccharides, lipids or other labile compounds.

The porous polymer monolith material is formed by a step-growth polymerisation process. Step-growth polymerisation typically refers to a type of polymerisation mechanism in which bi-functional or multifunctional monomers react to polymer chains which may have a high degree of crosslinking.

The step growth polymerisation process may comprise the polymerisation of one or more monomers having functional groups selected from at least one of hydroxyl, carboxylic acid, anhydride, acyl halide, alkyl halide, acid anhydride, acrylate, methacrylate, aldehyde, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, or azide functional groups. The monomers may have functional groups selected from at least one of hydroxyl, ester, amine, aldehyde, and carboxylic acid. In a further embodiment, the functional groups may include zwitteronic groups such as sulfoalkylbetaine-based zwitterionic compounds, for example N,N-dimethyl-N-methacryloxyethyl N-(3-sulfopropyl) ammonium betaine (SPE).

In one embodiment, the monomer is an acrylic acid monomer such as a methacrylate monomer, for example, hydroxy methacrylate [HEMA] and ethylene glycol dimethacrylate (EDMA).

In one embodiment, the porous polymer monolith material can be prepared by polymerizing a polymerisation mixture comprising one or more constituent monomers of the polymers in the presence of an initiator, and a porogen. The polymerisation mixture may be disposed on and/or in a support material which may include the porous polymer matrix material described herein and polymerisation can be initiated thereon so as to form a porous polymer monolith, which can then be washed with a suitable solvent to remove the porogen. The polymerisation mixture can also be prepared and polymerized first and then disposed upon a support material.

The polymerisation mixture can be comprised of a monomer (including crosslinking monomers) in an amount of about 10 to 60 vol %, and more particularly from about 15 to 40 vol %, about 45-85 vol % porogens and about 1 vol % initiator. In one embodiment, the polymerisation mixture is comprised of about 20-80% of a monomer (including crosslinking monomers), about 20-80 vol % porogens and about 1 vol % initiator. The ranges of each of the monomers, crosslinking monomers and porogens can be varied depending on the intended use.

Flat sheets of porous polymer monolith materials can be successfully fabricated, for example, by anchoring a thin sheet of monolith to a rigid glass plate by imparting methacryloyl functionalities to the surface of the glass. The methacryloyl functionalities participate in the polymerisation process resulting in the covalent attachment of the monolith to the glass slide during the polymerisation process.

In one embodiment, the porous polymer medium thereof is a sheet or film of up to about 1 mm in thickness, particularly about 300 to 900 µm in thickness, and more particularly about 500 to 700 µm in thickness. The polymer monolith may have a thickness of up to 500 µm, particularly about 200 to 400 μm. Other forms and thickness of monolith or monolith medium are contemplated and may be formed depending on the specific use, for example the type of post storage analysis contemplated.

Other preferred polymers include polymers with functional groups incorporated along the backbone of the polymer to facilitate further modification or interaction with blood or blood plasma. For example, a porous polymer monolith sheet can be configured to enable multiple blood spot samples to be provided thereon, and optionally configured to facilitate removal of excess monolith from around each blood spot sample.

Altering the porogens in the process of preparing the porous polymer monolith materials affects only the porous structure of the material while varying the other parameters modifies the composition and the rigidity of the material. Increasing the concentration of the non-solvent porogen induces precipitation early in the polymerisation procedure which typically results in material with a larger pore size. Thus the choice of porogenic solvents and their relative compositions are chosen to engineer a material of the desired porous structure.

The composition and percentage of porogenic solvent can be used to control the porous properties by changing or adjusting the percentage of the porogenic solvent mixture with a co-porogen, such as water or an organic solvent for example cyclohexanol, methanol, hexane, propanol or butanediol. This affects both median pore size and pore volume of the resulting monoliths. A broad range of pore sizes can easily be achieved by simple adjustments in the composition of porogenic solvent.

In one embodiment, the porogen used to prepare the porous polymer monolith may be selected from a variety of different types of materials. For example, suitable liquid porogens include organic solvents, aliphatic hydrocarbons, aromatic hydrocarbons, esters, amides, alcohols, ketones, ethers, solutions of soluble polymers, and mixtures thereof. The porogen is generally present in the polymerisation mixture in an amount of from about 40 to 90 vol %, more preferably from about 50 to 80 vol %. In a particular embodiment, the porogen or porogenic solvents include dodecanol, cyclohexanol, methanol, hexane, or mixtures thereof. In a preferred embodiment, the porogen is 1-decanol, cyclohexanol, methanol or hexane. In another particular embodiment, the porogenic solvent comprises at least 35% dodecanol in combination with cyclohexanol or methanol in combination with hexane.

The percent porosity is the percentage of pore volume in the total volume of the monolithic matrix. The term "pore volume" as used herein refers to the volume of pores in 1 g of the monolith. In one embodiment, the porous polymer monolith material has a macroporous structure having a percent porosity of about 45 to 85%, more particularly between about 60 and 75%. In another embodiment, the pore size of the porous polymer monolith can be in the range of 5 to 10,000 nm, 50 to 5,000 nm, 100 to 2,000 nm, 200 to 1000 nm. A smaller pore size correlates to a higher surface area which improves the loading capacity of body fluids such as blood and blood plasma. In another embodiment, the specific surface area of the porous polymer matrix when measured by nitrogen adsorption using BET isotherm (Atkins P, *Physical Chemistry*, Oxford University Press) is in the range of 0.5 to 1000 m$^2$/g, 1 to 500 m$^2$/g, 5 to 200 m$^2$/g, 10 to 100 m$^2$/g, 20 to 60 m$^2$/g, 30-50 m$^2$/g.

Polymerisation can be carried out through various methods of free radical initiation mechanisms including but not limited to gamma irradiation, thermal initiation, photoinitiation, redox initiation. In one embodiment, about 0.1-5 wt % (with respect to the monomers) of free radical or hydrogen abstracting photoinitiator can be used to create the porous polymer monolithic matrix. For example, 1 wt % (with respect to monomers) of a hydrogen abstracting initiator can be used to initiate the polymerisation process. Hydrogen abstracting photoinitiators may include benzophenone, 2,2-dimethoxy-2-phenylacetophenone (DMPAP), dimethoxyacetophenone, xanthone, and thioxanthone. If solubility of the chosen photoinitiator is poor, desired concentration of the initiator can be achieved by adding a surfactant that enables the homogenization of the initiator in emulsions with higher initiator concentration.

In another embodiment, whereby polymerisation is carried out by thermal initiation, the thermal initiator is generally a peroxide, a hydroperoxide, peroxo- or an azocompound selected from the group consisting of benzoylperoxide, potassium peroxodisulfate, ammonium peroxodisulfate, t-butyl hydroperoxide, 2,2'-azobisisobutyronitrile (AIBN), and azobisiocyanobutyric acid and the thermally induced polymerisation is performed by heating the polymerisation mixture to temperatures between 30° C. and 120° C.

In another embodiment, whereby polymerisation is initiated by a redox initiator, the redox initiator may be selected from the group consisting of mixtures of benzoyl peroxide-dimethylaniline, and ammonium peroxodisulfate-N,N,N', N'-tetramethylene-1,2-ethylenediamine.

The incorporation of functional groups into the porous polymer monolith material increases the polarity of the surface and thus the wettability. As blood is composed predominantly of water, the incorporation of the polar monomer into the monolith is beneficial for the adsorption of the blood.

Varying the type and amounts of porogenic solvents can provide control over the pore size distribution of the monoliths, which can be examined by mercury intrusion porosimetry (MIP). With a polar monomer, increasing the concentration of a less polar porogen, such as 1-dodecanol, typically provides monoliths with larger pores.

It was found that increasing the percentage of dodecanol between 38-100% of porogenic solvent in a mixture of dodecanol and cyclohexanol maintained the pore size distribution at approximately 600 nm. A binary porogenic solvent of methanol and hexane at equal ratios was employed to achieve large pores in the monolith. A pore size distribution may be achieved around 7000 nm. Monoliths with a smaller pore size are more reproducible, for example a monolith containing a binary porogenic solvent of 40% dodecanol and 20% cyclohexanol.

The visual appearance of the monolith is considered to be a reliable indicator of the pore size due to light scattering. The monoliths studied appeared chalky which indicated a macroporous material (i.e. above about 50 nm pore size). Analysis by MIP confirmed this, with the median pore diameter measured at about 600 nm and the monolith porosity being 68%. The specific surface area for the monolith was determined by BET analysis.

Various types of step growth polymers may be used including groups enabling various types of branching, such as at least one of star, comb, brush, ladders, and dendrimer type monomer, co-monomer or polymer group.

Support Material

The support materials of the porous polymer monolith material may be aflexible, semi-rigid or rigid film, membrane or backing layer. This association between the support material and the polymer matrix may be by attachment, removable attachment, or non-attachment. The support material may include the porous polymer matrix material described herein.

Optional Additives

The porous polymers materials according to any of the above described embodiments may also include other additives such as rheology modifiers, fillers, tougheners, thermal or UV stabilizers, fire retardants, lubricants, surface active agents. The additive(s) are usually present in an amount of less than about 10% based on the total weight of the activation treatment or the combination of solvent(s), agent(s) and additive(s). Examples include:

(a) rheology modifiers such as hydroxypropyl methyl cellulose (e.g. Methocell 311, Dow), modified urea (e.g. Byk 411, 410) and polyhydroxycarboxylic acid amides (e.g. Byk 405);

(b) film formers such as esters of dicarboxylic acid (e.g. Lusolvan FBH, BASF) and glycol ethers (e.g. Dowanol, Dow);

(c) wetting agents such as fluorochemical surfactants (e.g. 3M Fluorad) and polyether modified poly-dimethyl-siloxane (e.g. Byk 307, 333);

(d) surfactants such as fatty acid derivatives (e.g. Bermadol SPS 2543, Akzo) and quaternary ammonium salts;

(e) ispersants such as non-ionic surfactants based on primary alcohols (e.g. Merpol 4481, Dupont) and alkylphenol-formaldehyde-bisulfide condensates (e.g. Clariants 1494);

(f) anti foaming agents;

(g) anti corrosion reagents such as phosphate esters (e.g. ADD APT, Anticor C6), alkylammonium salt of (2-benzothiazolythio) succinic acid (e.g. Irgacor 153 CIBA) and triazine dithiols;

(h) stabilizers such as benzimidazole derivatives (e.g. Bayer, Preventol BCM, biocidal film protection);

(i) leveling agents such as fluorocarbon-modified polymers (e.g. EFKA 3777);

(l) pigments or dyes such as fluorescents (Royale Pigment and chemicals);

(k) organic and inorganic dyes such as fluoroscein; and (l) Lewis acids such as lithium chloride, zinc chloride, strontium chloride, calcium chloride and aluminium chloride.

(m) Suitable flame retardants which retard flame propagation, heat release and/or smoke generation which may be added singularly or optionally include:

Phosphorus derivatives such as molecules containing phosphate, polyphosphate, phosphites, phosphazine and phosphine functional groups, for example, melamine phosphate, dimelamine phosphate, melamine polyphosphate, ammonia phosphate, ammonia polyphosphate, pentaerythritol phosphate, melamine phosphite and triphenyl phosphine.

Nitrogen containing derivatives such as melamine, melamine cyanurate, melamine phthalate, melamine phthalimide, melam, melem, melon, melam cyanurate, melem cyanurate, melon cyanurate, hexamethylene tetraamine, imidazole, adenine, guanine, cytosine and thymine.

Molecules containing borate functional groups such as ammonia borate and zinc borate.

Molecules containing two or more alcohol groups such as pentaerythritol, polyethylene alcohol, polyglycols and carbohydrates, for example, glucose, sucrose and starch.

Molecules which endothermically release non-combustible decomposition gases, such as, metal hydroxides, for example, magnesium hydroxide and aluminum hydroxide.

Expandable graphite

The additive may be selected from one or more of a silica powder, silica gel, chopped glass fiber, controlled porous glass (CPG), glass beads, ground glass fiber, glass bubbles, kaolin, alumina oxide, nanosintered diamond. The additive may be fibreglass.

In an embodiment of the porous polymer matrix material, other additives may include lubricants, fibres, colourants, fillers, functional additives, active agents (e.g. antimicrobial), or antistatic agents. The functional additive may comprise a compound having functionality selected from one or more of hydroxyl, carboxylic acid, anhydride, acyl halide, alkyl halide, aldehyde, alkene, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, or azide functional group. The functional additive may comprise a compound having an hydroxyl, amine, aldehyde, or carboxylic acid functional group. The active agent may be a drug, hydrophilic moiety, catalyst, antibiotic, antibody, antimycotic, carbohydrate, cytokine, enzyme, glycoprotein, lipid, nucleic acid, nucleotide, oligonucleotide, peptide, protein, ligand, cell, ribozyme, or a combination thereof.

Preparation, Storage and Analysis of Body Fluids

The porous polymer materials described herein are used for storing biological fluid samples or body fluid samples, particularly blood and blood plasma for future analysis (e.g. of analytes including pharmaceutical agents or metabolites thereof). Blood or blood plasma samples can be applied directly to the porous polymer materials. The combination of sample and porous polymer material is then dried to form a solidified sample that is adsorbed or adhered to the storage medium.

The body fluid sample typically comprises genetic material (e.g. DNA and RNA) and may be obtained from any source, for example, physiological/pathological body liquids (e.g., blood, urine, secretions, excretions, exudates and transudates) or cell suspensions (e.g., blood, lymph, synovial fluid, semen, saliva containing buccal cells).

The porous polymer materials provide for storage or subsequent analysis of a stored sample. The porous polymer materials can be composed of a solid matrix comprising functionality, and/or a composition or one or more active agents, which can protect against degradation of genetic material stored on the porous polymer materials or facilitate inactivation of microorganisms (e.g. microorganisms associated with a sample which may degrade the sample or may be potentially pathogenic to human handlers), facilitate the extraction of particular analytes, or facilitate matrix elimination to aid identification and analysis of analytes.

Dried body fluid samples on the porous polymer materials can be analysed at a later stage, for example used for pharmacokinetic analysis of pharmaceutical agents present in blood and plasma samples. Following drying of body fluid samples on the porous polymer materials, they are particularly suitable for storage and transportation of such samples, particularly whole blood and plasma samples, because at this stage they are considered to be relatively safe to handle and not infectious (e.g. with respect to infections diseases that may be carried in the blood such as HIV).

The porous polymer materials may be configured or adapted to enable storage of body fluids for many years, including any one of the following time periods at least a day, a week, a month, 6 months, one year, two years, 5 years, 10 years, 20 years, or up to 50 years or more.

In an embodiment, the long term storage of a body fluid on the porous polymer material can be facilitated by encasing the porous polymer materials in particular the porous polymer monolith materials in a protective material, for example a plastics material such as polystyrene, which can be subsequently removed when access to the stored sample is required.

In the storage of blood, the blood sample can be applied as a blood spot to the porous polymer materials. Functionality, components, or one or more agents, may be added to or incorporated into the porous polymer materials to provide particular optional properties suited for various purposes (e.g. for denaturing proteins, eliminating matrix or reducing or removing any pathogenic organisms in the sample). At the same time, the blood (and genetic material and/or analytes therein) can be protected from degradation factors and processes so that the relatively stable dried blood sample can then be stored and transported to a diagnostic laboratory. The analytes or genetic material can be extracted, analysed or used in situ on the porous polymer materials.

Active agents or a composition used with the porous polymer materials can comprise, for example, a monovalent weak base (such as "Tris", tris-hydroxymethyl methane, either as the free base or as the carbonate), a chelating agent (such as EDTA, ethylene diamine tetracetic acid), an anionic detergent (such as SDS, sodium dodecyl sulphate), guanidine, or uric acid or a urate salt. Other agents may include retaining agents to reduce the loss of analytes in subsequent analysis, which may occur during storage or pre-analysis treatment procedures.

Monomers with specific functionality can be incorporated to aid the elimination of the biological matrix from the sample. The ability to functionalise the surface of the paper based medium is limited, whilst simple protocols for the modification of polymeric media to incorporate functionality are well established.

In another embodiment, functionality can be incorporated into the porous polymer material for in situ elimination of undesirable components in blood that impede the detection of specific analytes, for example pharmaceutical agents or other low or small molecular weight compounds. In one particular embodiment, the surface area of the porous polymer material can be provided with ion exchange properties to facilitate the adherence thereon of selected pharmaceutical agents or non-adherence of selected contaminants present in the body fluid. The porous polymer material may therefore be used to analyse body fluids dried thereon without the need for chemical based post or pre-treatment. In another particular embodiment, the ion exchange properties may be provided by functional groups present on a monomer or co-monomer from which the porous polymer material is formed, and/or a post polymerisation surface modification comprising co-polymerisation grafting or other chemical modification. The chemical modification may be photografting, for example as described in U.S. Pat. No. 7,431,888, which is herein incorporated by reference. The photografting may be by UV or gamma irradiation. The chemical modification may be chemical C—H activation, for example as may be mediated by transition metal complexes.

Grafting is a way of tailoring surface chemistry. Several methods have been used to graft polymers onto thermoplastic polymer surfaces including such widely diverse methods as flame treatment, corona discharge treatment, plasma treatment, use of monomeric surfactants, acid treatment, free radical polymerization and high energy radiation. See, for example, Uyama, Y. et al., Adv. Polym. Sci. 1998, 137, 1.

Attachment of chains of polymer to the sites at the pore surface within a generic monolith or porous polymer material provides multiple functionalities emanating from each individual surface site and dramatically increases the density of surface functionalities. Examples of grafting and functionalization of porous polymer materials including porous polymer monolith materials using free radical polymerization initiation can be found in the art. Viklund, C. et al. in Macromolecules 2000, 33, 2539, incorporate zwitterionic sulfobetaine groups into porous polymeric monoliths. Peters, et al. have previously shown in U.S. Pat. No. 5,929,214, that thermally responsive polymers may be grafted to the surface of pores within a polymer monolith by a two-step grafting procedure which entails (i) vinylization of the pores followed by (ii) in situ free radical polymerization of a selected vinyl monomer or mixture of selected monomers. The thermally responsive polymer changes flow properties through the pores in response to temperature differences.

Surface photografting with vinyl monomers has been used for functionalization of polymer fibers, films and sheets as for example described by Ranby B. et al., in Nucl. Instrum. Methods Phys. Res. Sect. B, 1991, 151, 301. Photografting can be used for modification of flat two dimensional surfaces or for three dimensional highly crosslinked porous polymer monoliths.

In an embodiment, the chemical modification of the surface of the porous polymer material is by UV initiated photografting. For example UV initiated photografting mediated by a hydrogen abstracting photoinitator, which may be used to modify the channel surface, to create the porous monolith or material and to modify the monolith or material in selected regions. Modification and surface functionalization of the porous polymer materials can be accomplished by photoinitiated grafting within a specified space (i.e. a microfluidic channel or a portion thereof), which permits the layering and patterning of different functionalities on the surface of polymers.

Prior to a blood sample being adsorbed or adhered to the medium, the blood sample can be lysed to facilitate adherence of the sample to the medium. The pore size of the porous polymer material medium can be provided to be at or above the diameter of red blood cells (typically about 6,000 to 8,000 nm) to facilitate adherence of the blood sample to the medium.

In an embodiment, there is provided a method of storing a body fluid for future analysis comprising applying a body fluid sample to a porous polymer material medium and drying the body fluid such that the sample at least partially solidifies and adsorbs or adheres to the porous polymer material medium.

In another embodiment, a method of storing a body fluid for future analysis can comprise:

applying one or more body fluid samples to one or more regions of the porous polymer material medium;

partially drying the one or more samples applied to the medium;

storing the one or more samples applied to the one or more regions of the medium.

In another embodiment, a method of storing a body fluid for future analysis can comprise:

applying one or more body fluid samples to one or more regions of the porous polymer material medium as described herein;

partially drying the one or more samples applied to the medium;

separating any one or more regions of the medium having sample applied thereto from regions without sample applied thereto;

storing the one or more samples applied to the one or more regions of the medium.

In another embodiment, a method of storing a body fluid for future analysis can comprise:

applying one or more body fluid samples to one or more regions of the porous polymer material medium as described herein;

partially drying the one or more samples applied to the medium;

separating any one or more regions of the medium having sample applied thereto from regions without sample applied thereto;

further drying the one or more samples applied to the one or more regions of the medium; and storing the one or more samples applied to the one or more regions of the medium.

The separating of any one or more regions of the porous polymer material having sample applied thereto from regions without sample applied thereto, may comprise substantially removing any medium not having body fluid applied thereto from around the sample, for example trimming or cutting away medium at or near the perimeter of the sample. The medium may be trimmed or cut away from around the sample such that the sample substantially covers the surface of the region to which the sample was applied, for example by using a hole punch of narrower diameter than a blood spot sample. In other words, the blood spot sample can extend at or near to the outer edge of the porous polymer material medium region to which the sample is applied. One advantage of this embodiment is that cracking of the sample can be reduced or prevented during the drying of the sample. The removal of any medium that is not contacted by the sample can facilitate adherence and non-cracking of the sample upon drying. Typically the sample is cut away or punched out from excess medium.

The samples applied to the medium are typically about 1 to 20 mm in diameter, and may be about 2-15 mm or 5-10 mm in diameter, for example generally spherical of a size of 10 to 100 mm$^2$. For example, the one or more samples can be selected from any one of the following sizes (mm$^2$) 1, 10, 20, 30, 40, 50, 60, 70, 80, 90, or 100. In another embodiment, the one or more regions can be selected from any one of the following sizes (mm$^2$) 1, 10, 20, 30, 40, 50, 60, 70, 80, 90, or 100. It will be appreciated that depending on the procedure, application or equipment used, variability may be associated with the application of samples to the medium, and ranges above, below or between these sizes also fall within the scope of the invention. The medium can also be sized or shaped to facilitate the substantial coverage of its surface with a body fluid sample, for example by providing one or more individual regions of the medium on a support material (e.g. an array), the regions being of a size that enables application of a sample thereto that can cover the surface thereof. Various patterns and arrangements of one or more samples to one or more regions also fall within the scope of these embodiments. For example, an array of body fluid samples can be applied to the medium, such as by providing an individually separated array of 5×5 samples of about 20 mm$^2$. In another embodiment, the array of samples may be applied to and/or cut away from a single medium, or applied to an array of one or more individual regions of medium.

The drying of the body fluid, such as blood or blood plasma, can be enhanced by application of at least one of elevated temperature, forced convection or reduced pressure. The elevated temperature may be in a temperature range above ambient but below the temperature at which the integrity of storage medium or sample is compromised. In a particular embodiment the elevated temperature is in the range of 30 to 150° C., 40 to 120° C., and more particularly about 60 to 100° C., or 30° C. and above, 50° C. and above, 70° C. and above, 90° C. and above, 110° C. and above, or 130° C. and above. In one particular embodiment the elevated temperature is above about 90° C., which for certain types of monolith mediums and samples may enhance future analysis of the samples or prevent cracking of the samples upon drying. Typically the samples can be dried in about 10 to 20 minutes under the elevated temperatures. In a particular embodiment, the reduced pressure is in the range of 5 to 760 mmHg. Reduced pressure can be applied by way of vacuum apparatus.

There is also provided a method of analysis involving the identification and detection of an analyte from a stored body fluid sample adsorbed or adhered to a porous polymer material medium.

In one embodiment, the stored body fluid sample can be analysed without pre-treatment and/or removal from the porous polymer material medium. In other words, the samples stored on the medium can be used directly in analysis without further modification. The analytes can include small molecules and low molecular weight compounds present in blood or blood plasma samples, for example, pharmaceutical agents including new chemical entities (NCEs) and any metabolites thereof, peptides, proteins, oligonucleotides, oligosaccharides, lipids or other labile compounds. In another embodiment, the analysis involves the simultaneous analysis of at least two analytes. In a particular embodiment, the at least two analytes comprise an NCE and a metabolite thereof.

Porous Polymer Materials for Selective Extraction and Matrix Elimination

Ion-exchange functionality may be incorporated into the porous polymer materials to facilitate selective extraction of particular analytes, such as pharmaceutical agents or NCEs, and to facilitate matrix elimination. Both co-polymerisation and surface modification techniques can be employed to incorporate functionality into the polymer materials.

Typically the porous polymer materials have a hydrophilic surface to facilitate adsorption of the body fluid. Functionality that can be incorporated into the porous polymer materials to facilitate in situ sample cleanup or matrix elimination, facilitate specific extraction (e.g. of analytes), or facilitate bioanalysis. Strong cation exchange (SCX) functionality may be provided, for example, by incorporating sulphonic acid type surface groups (e.g. HEMA-co-SPMA), weak cation exchange (WCX) functionality may be provided by carboxylic acid surface groups, strong anion exchange (SAX) may be provided by quaternary amine surface groups, and weak anion exchange (WAX) may be provided by tertiary amine surface groups.

Solid phase extraction (SPE) methods involve sample preparation to purify and concentrate analytes from a matrix by the sorption onto a medium followed by the elution with an appropriate solvent. The analyte partitions between the solid phase and the solvent and only those analytes with a high affinity for the solid phase are retained. Following matrix elimination the analyte can then be eluted from the solid phase and analysed.

Polymer materials such as monoliths with acidic functional groups can be fabricated for the selective extraction of NCEs containing basic functional groups while polymer monoliths with basic functionality allow the selective extraction of NCEs that are somewhat acidic. The incorporation of functionality into porous polymeric materials is generally well established and can be achieved using several different strategies.

Two possible methods for the incorporation of specific functionalities into the porous polymeric monolithic medium are either by incorporation of a functional monomer directly into the polymerisation mixture or by a post-polymerisation of the monolithic scaffold. The approach of introducing the functional monomer directly into the polymerisation mixture along with the structural monomers is by far the simplest approach as no subsequent modifications are required. However, as the functional monomer is part of the polymerisation mixture it is possible that a large portion of the ionisable groups will be trapped within the bulk of the media and not available at the surface of the monolith for interaction with the NCE.

The second approach is a post-polymerisation reaction which imparts the functional groups directly to the surface of the material by covalent attachment. The material can be optimized separately meaning that a variety of functionalities can be imparted. The advantage of employing a post polymerisation reaction is that the functionality is imparted directly onto the surface of the material meaning that it is easier to synthesise higher capacity materials for increased sample loading. Surface functionality can be imparted using two very different approaches; the first is an alternation of the surface chemistry though a chemical reaction. This approach requires the structural monomers to include reactive groups. The second option is to complete a second polymerisation reaction on top of the previously formed material; this technique is known as surface grafting.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention will now be described with reference to the following non-limiting examples.

EXAMPLES

Example 1—Preparation and Use of Porous Polymer Matrix Medium

The macroporous structure of all polymer materials was measured by mercury intrusion porosimetry using a Micromeritics AutoPore IV 9505 (Norcross, Ga., USA) porosimeter. Specific surface area was determined by the Brunauer-Emmet-Teller (BET) [Brunauer S et al, *Journal of the American Chemical Society*, 1938. 60: p. 309-319] method using a Micromeritics TriStar II 3020 automated nitrogen sorption/desorption instrument.

An OAI LS30/5 Deep UV irradiation system (San Jose, Calif., USA) with a 500 W HgXelamp was utilised for all UV exposures. Lamp calibration to 20.0 mW/cm$^2$ was performed with an OAI Model 306 intensity meter with a 260 nm probe head.

Porous high density polyethylene membranes (X-4913, 90-130 μm median pore diameter) were obtained from Porex (GA, USA).

Preparation of Modified Medium

The porous high density polyethylene membrane was immersed in a deaerated solution consisting of 15 wt % of 2-Acrylamido-2-methyl-1-propanesulfonic Acid, 0.22 wt % benzophenone, 63.6 wt % tert-butyl alcohol and 21.1 wt % water. The matrix was left to stand in this solution for at least 10 minutes, excluded from air. The matrix was covered with a glass microscope slide and grafting was achieved by UV irradiation with an irradiation time of 15 minutes. The matrix was then washed with water by constant agitation in a rocking bath for at least 2 hours and then allowed to dry at room temperature.

Use of Medium for DBS

To demonstrate the potential of the modified porous polymer matrix as a medium or sorbent for the storage of whole blood, 15 μL aliquots of whole human blood were spotted directly onto both the unmodified and modified matrix. The blood did not penetrate the unmodified matrix, drying as irregular sized spots. On the modified matrix, the blood penetrated the entire thickness of the matrix (~2 mm) and excellent uniformity was displayed for both spot size and shape. The blood spot was touch dry on this matrix within 1 hour at room temperature.

Example 2—Preparation of Porous Polymer Monolith Material on a Support Membrane

The macroporous structure of all polymer materials was measured by mercury intrusion porosimetry using a Micromeritics AutoPore IV 9505 (Norcross, Ga., USA) porosimeter. Specific surface area was determined by the Brunauer-Emmet-Teller (BET) [Brunauer S et al, *Journal of the American Chemical Society*, 1938. 60: p. 309-319] method using a Micromeritics TriStar II 3020 automated nitrogen sorption/desorption instrument. All monoliths were degassed in a Micromeritics vacprep at a temperature of 50° C. for 24 hours.

Figure 1:
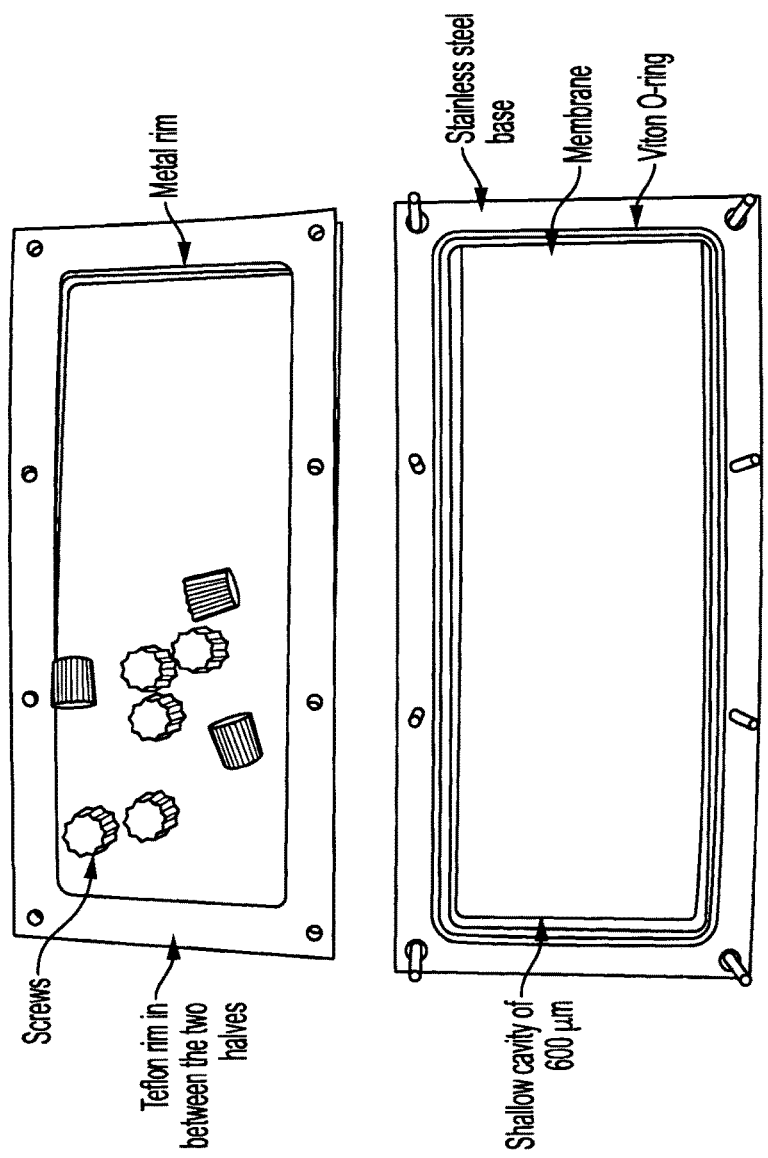
FIG. 1 is a drawing showing the container used to prepare the porous polymer monolith material on a support membrane of Example 2.

Flat sheet monolith on a support membrane was prepared using a rectangular sandwich container as shown in FIG. 1. The sandwich container is made of stainless steel and has a dimension of (W×L×H) 11.3×24.5×2.3 cm. It consists of two halves; a base with a thickness of 1.4 and an upper rectangular rim which is 0.45 cm thick. An empty space of 8.1×21.5 cm of the rim allows the exposure of UV in the middle. The central part of the base is a shallow cavity which has a dimension of (W×L) 8×21.5 cm and a depth of 600 μm. A Viton O-ring of 8.8×22.0 cm used to form a barrier along the edges of the shallow cavity to prevent the solution from leaking out. A piece of glass plate of 9.5×22.8 cm and 0.4 cm in thickness placed in between the two halves of the container to seal the cavity and to form monolith inside.

Preparation of Polymerization Mixture

The polymerization mixture (17.58 g) was prepared by weighing the appropriate initiator, monomers, crosslinking monomer and porogens in a vial. The polymerization mixture consisted of 19.3% (w/w) monomer (2-hydroxyethyl methacrylate, HEMA), 19.3% (w/w) crosslinking monomer (ethylene glycol dimethacrylate, EDMA), 30.7% (w/w) of each porogen (methanol and n-hexane) mixed with a UV initiator (2,2-dimethoxy-2-phenylacetophenone (DMAP)) to give a clear organic solvent mixture. The amount of initiator used corresponded to 1% (w/w) of the total amount of monomer and crosslinking monomer. The mixture was sonicated for 10 mins in order to ensure dissolution of the components.

Preparation of Polymer Monolith on the Membrane

1. A support membrane with a size of 7×20.5 cm was placed on the central part of the cast. The support membrane was a non-woven polyester fibre (OTH001 marketed by BMP America) having a thickness of 0.59 mm and a weight of 130 g/m$^2$.

2. The polymerization mixture was injected into the shallow cavity with a Pasteur pipette just enough to wet the whole sheet of the membrane.

3. The cast was covered with a piece of glass plate of 9.5×22.8 cm and 0.4 cm in thickness in between the two halves of the container.

4. The two halves were fastened together with 8 screws that distribute 7.5 cm from one another.

5. The polymerization mixture was injected via a syringe fitted with a 25 gauge syringe needle in the container until the whole space was occupied with the mixture.

6. With the solution in place and the two halves of the sandwich container secured, the container was irradiated under UV for 50 min using a Spectrolinker™ XL-1500 Series (Spectronics Corporation, Westbury, N.Y., USA).

7. After polymerization, the support membrane with the monolith was separated from the cast and transferred to a container with methanol and washed overnight on a rocker (Gyro-Rocker STR9, STUART instruments, Bibby Scientific Limited, UK).

8. The washed support membrane with the monolith flat sheet was dried in a vacuum oven at ambient temperature overnight.

Use of Polymer Monolith for Dried Blood Spot (DBS) Sampling Technology for Use in Drug Discovery (3 mm Spot, Nominal Concentration 2500 ng/ml)

The objective of this example was to test the diffusion properties and variability of the haematocrit levels of DBS using the polymer monolith material and support membrane prepared as described above.

| Compounds: | Card type: | Hematocrit level: |
|---|---|---|
| Fluconazole–I.S. D8-fluconazole | Example 2 | HT1-20% |
| Gabapentin–I.S. D4-Gabapentin | Whatman FTA DMPK-C ™ | HT2-30% |
| Ibuprofen–I.S. D3-ibuprofen | Agilent Bond Elut DMS ™ | HT3-45% Normalized HT4-60% HT5-80% |

Figure 2:
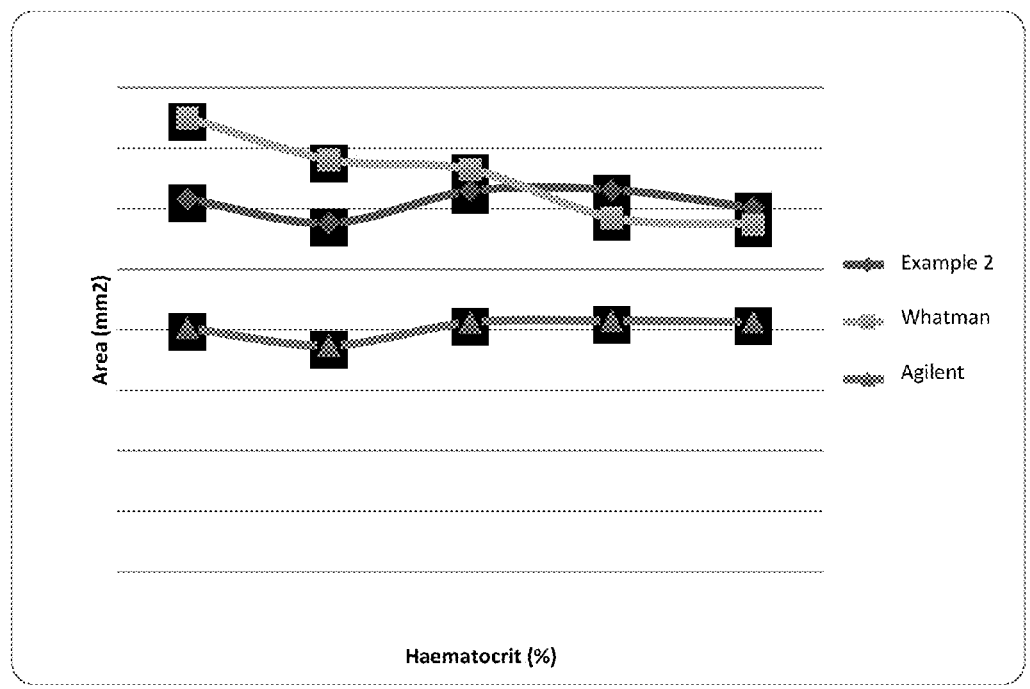
FIG. 2 is a graph showing the effect of human blood haematocrit on an area of dried blood spots or Example 2, Whatman FTA DMPK-C™ cards and Agilent Bond Elut DMS™ cards.

Effects of Human Blood Haematocrit on Area of Dried Blood Spots on Example 2, Whatman FTA DMPK-C Cards™ and Agilent Bond Elut DMS™ Cards The largest difference between haematocrit levels for Example 2, Whatman and Agilent were 9%, 26% and 10%, respectively. The spot areas were measured by integration using the program ImageJ. Pixel counts were converted to mm$^2$. The difference was 9%, 14% and 9% at either extreme of Example 2, Whatman and Agilent cards, respectively. This measurement is more accurate because we use ImageJ to measure the area of the whole blood spot rather than using the diameter of the blood spot to calculate the area (the blood spot may not be in round shape). The results are set out in Table 1 below and represented graphically in FIG. 2.

TABLE 1

| | HCT 20 | HCT 35 | HCT 45 | HCT 65 | HCT 80 | |
|---|---|---|---|---|---|---|
| | Example 2 | | | | | |
| Area (mm$^2$) | 30.80 | 28.81 | 31.47 | 31.57 | 30.08 | |
| % RE | 10.8% | 7.0% | 3.2% | 2.8% | 6.6% | |
| CV from HCT 45 | −2.1% | −8.5% | | 0.3% | −4.4% | 9% |
| | Whatman | | | | | |
| Area (mm$^2$) | 37.50 | 34.06 | 33.24 | 29.26 | 28.72 | |
| % RE | 1.3% | 1.7% | 2.4% | 3.5% | 1.2% | |
| CV from HCT 45 | 12.8% | 2.4% | | −12.0% | −13.6% | 26% |
| | Agilent | | | | | |
| Area (mm$^2$) | 20.14 | 18.70 | 20.62 | 20.75 | 20.64 | |
| % RE | 3.8% | 2.2% | 2.1% | 1.6% | 1.6% | |
| CV from HCT 45 | −2.3% | −9.3% | | 0.6% | 0.1% | 10% |

Figure 3:
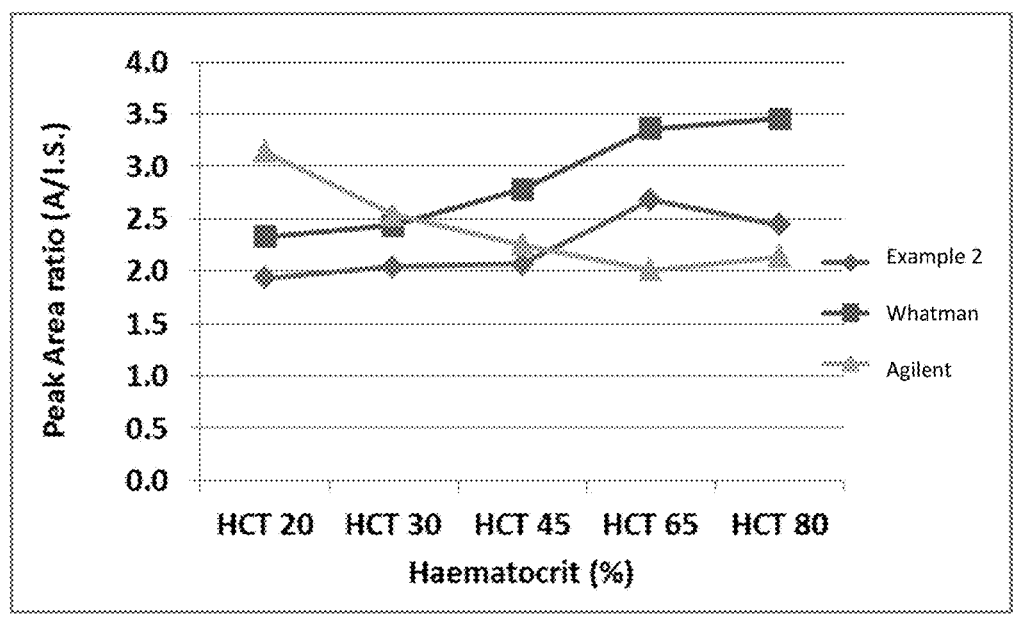
FIG. 3 is a graph showing the effect of ovine blood haemacrit on an area of dried blood spots on Example 2, Whatman FTA DMPK-C™ cards and Agilent Bond Elut DMS™ cards on responses to Gabapentin.
Figure 4:
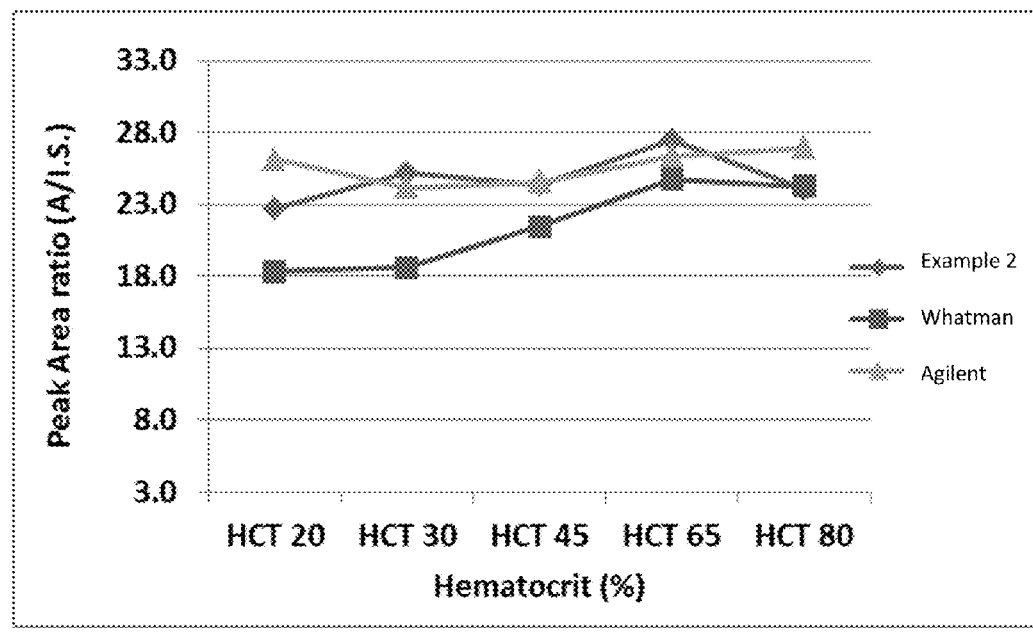
FIG. 4 is a graph showing the effect of ovine blood haematocrit on an area of dried blood spots on responses to Fluconazole.
Figure 5:
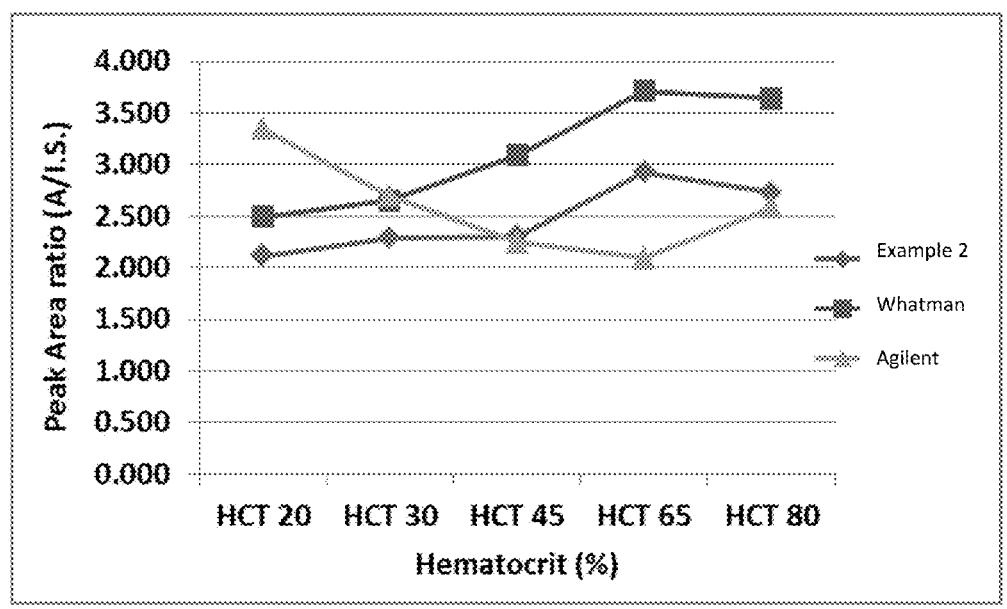
FIG. 5 is a graph showing the effect of ovine blood haematocrit on an area of dried blood spots on responses to Ibuprofen.

The effect of human blood haematocrit on responses to Gabapentin, Fluconazole and Ibuprofen are shown in FIGS. 3-5. The percentage difference from HCT 45% were over 15% for Gabapentin and Ibuprofen on Example 2. Again, higher percentage errors were observed when HCT 20 and HCT 80 were used on Whatman. The Agilent card was susceptible to low haematocrit levels of HCT 20 and HCT 30 for Gabapentin and Ibuprofen. Overall, lower percentage errors were observed using Fluconazole on three card types.

Use of Polymer Monolith for Dried Blood Spot (DBS) Sampling Technology for Use in Drug Discovery The objective of this example was to demonstrate the consistency (or lack) of recovery of the analyte from different locations within the Dried Blood Spot, i.e. to demonstrate the homogeneity of the DBS.

Compounds:
Fluconazole—I.S. D8-fluconazole
Gabapentin—I.S. D4-Gabapentin
Ibuprofen—I.S. D3-ibuprofen
Card type:
Example 2A and 2B
Whatman FTK DMPK-C™
Agilent Bond Elut DMS™

Disk size 1.5 mmA 1.5 mm punch was taken out of a 20 ul blood spot in the marked location shown in FIG. 9. Concentration=2500 ng/mL (3 times higher for Ibuprofen) in blood. The first one is normalized and compared against the other punches. The ratio of peak area of compounds vs internal standard was used. CV was calculated from the center.

Example 2A is the porous polymer monolith on a support membrane of Example 2 which is 800 microns thick having a membrane of 400 microns thick and a monolith of 400 microns thick.

Example 2B is the porous polymer monolith on a support membrane of Example 2 which is 640-700 microns thick having a membrane of 400 microns thick and a monolith of 240-300 microns thick.

Procedure

20 μL of 2500 ng/mL blood samples containing Gabapentin, Fluconazole and Ibuprofen (7500 ng/mL) were spotted onto the different card types.

The spots were dried for an hour on Examples 2A and 2B and 2 hours for the other card types.

A 1.50 mm disk was punched from each dried spot and placed into an Eppendorf tube.

300 µL of 0.1% formic acid in 80% methanol (with 5 ng/mL of deuterated internal standard mix) was added to the samples and then vortexed and soaked for ~2 hours (or sonicated if possible).

The samples were centrifuged (14000 rpm×5 min) and the supernatant collected 250 uL and transfer to 0.5 mL tube The samples were evaporated to dryness in a vacuum oven at 35° C. overnight.

The samples were reconstituted in 200 uL of water:methanol (9:1) or (60 ng/mL sample and 7.5 ng/mL I.S.), centrifuged (14000 rpm×5 min) and then transferred 100 uL to 250 uL sample vials for analysis.

These results are set out in Table 2 below.

TABLE 2

| | | | Position | | | | |
|---|---|---|---|---|---|---|---|
| | | | 1 | 2 | 3 | 4 | 5 |
| Gabpentinn | Example 2A | Average Peak area ratio (n = 4) | 0.5556 | 0.576 | 0.572 | 0.605 | 0.619 |
| | | CV % | 14% | 7% | 7% | 4% | 7% |
| | | CV from center | | 4% | 3% | 9% | 11% |
| | Example 2B | Average Peak area ratio (n = 4) | 0.471 | 0.492 | 0.483 | 0.491 | 0.468 |
| | | CV % | 7% | 9% | 4% | 8% | 9% |
| | | CV from center | | 5% | 3% | 4% | −1% |
| | Whatman | Average Peak area ratio (n = 4) | 0.727 | 0.813 | 0.787 | 0.813 | 0.858 |
| | | CV % | 3% | 8% | 6% | 3% | 9% |
| | | CV from center | | 12% | 8% | 12% | 18% |
| | Agilent | Average Peak area ratio (n = 4) | 0.461 | 0.676 | 0.703 | 0.969 | 1.014 |
| | | CV % | 41% | 34% | 21% | 32% | 13% |
| | | CV from center | | 47% | 53% | 110% | 120% |
| Fluconazole | Example 2A | Average Peak area ratio (n = 4) | 7.527 | 7.474 | 7.546 | 7.599 | 8.011 |
| | | CV % | 7% | 4% | 2% | 3% | 5% |
| | | CV from center | | −1% | 0% | 1% | 6% |
| | Example 2B | Average Peak area ratio (n = 4) | 5.725 | 5.736 | 5.920 | 5.664 | 5.634 |
| | | CV % | 4% | 7% | 3% | 9% | 8% |
| | | CV from center | | 0% | 3% | −1% | −2% |
| | Whatman | Average Peak area ratio (n = 4) | 6.171 | 7.087 | 6.617 | 7.226 | 7.582 |
| | | CV % | 7% | 9% | 4% | 5% | 6% |
| | | CV from center | | 15% | 7% | 17% | 23% |
| | Agilent | Average Peak area ratio (n = 4) | 7.019 | 7.993 | 8.180 | 9.683 | 9.990 |
| | | CV % | 19% | 14% | 8% | 18% | 10% |
| | | CV from center | | 14% | 17% | 38% | 42% |
| Ibuprofen | Example 2A | Average Peak area ratio (n = 4) | 1.989 | 1.920 | 1.892 | 2.127 | 2.074 |
| | | CV % | 16% | 5% | 6% | 11% | 5% |
| | | CV from center | | −3% | −5% | 7% | 4% |
| | Example 2B | Average Peak area ratio (n = 4) | 1.795 | 1.747 | 1.724 | 1.715 | 1.700 |
| | | CV % | 9% | 12% | 5% | 6% | 10% |
| | | CV from center | | −3% | −4% | −4% | −5% |
| | Whatman | Average Peak area ratio (n = 4) | 2.535 | 3.020 | 2.873 | 2.989 | 3.191 |
| | | CV % | 3% | 9% | 3% | 6% | 10% |
| | | CV from center | | 19% | 13% | 18% | 26% |
| | Agilent | Average Peak area ratio (n = 4) | 2.034 | 2.537 | 2.755 | 3.355 | 3.486 |
| | | CV % | 28% | 28% | 16% | 25% | 12% |
| | | CV from center | | 25% | 35% | 65% | 71% |

The peak area ratio for the individual positions are mostly reproducible except for the spots on the Agilent card. Deviations of the peak area ratio from the centre punch were not consistent especially on the Agilent card.

Figure 6:
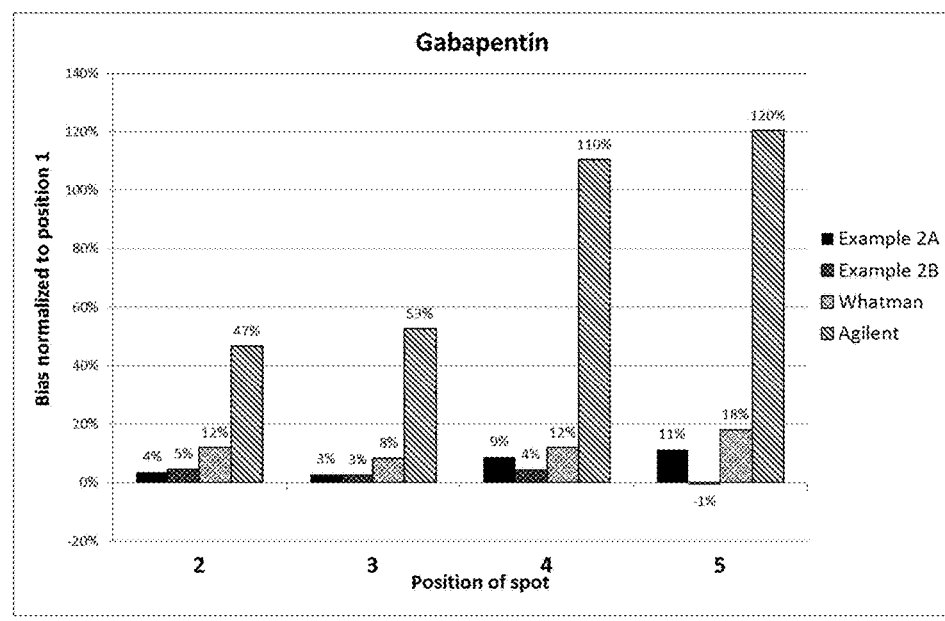
FIG. 6 is a graph showing the consistency of the recovery of Gabapentin from different positions (2, 3, 4 and 5) within the dried blood spots normalized to position 1.

The results are shown graphically in FIGS. 6-8.

What is claimed is:

1. A method of storing a whole blood sample for future analysis comprising applying the whole blood sample directly to a porous polymer monolith material medium and drying the whole blood sample such that the whole blood sample at least partially solidifies and adsorbs or adheres to the porous polymer monolith material;

wherein the porous polymer monolith material medium is formed by a step-growth polymerization process, wherein the medium additionally comprises one or more supporting layers comprising a porous polymer matrix material, wherein the porous polymer matrix material of each of the one or more support layers is selected from a polyether, polyester, polycarbonate, polyanhydride, polythiophene polymer, and an epoxy resin, wherein the medium allows storage of the whole blood sample for at least one day, wherein the whole blood sample is applied directly to the medium, with the proviso that the porous polymer monolith material is polymerized onto or sits on the one or more supporting layers comprising the porous polymer matrix material without one or more intervening layers of functionality formed by photoinitiated grafting.

2. A method of storing a whole blood sample for future analysis comprising:
applying one or more whole blood samples directly to one or more regions of a porous polymer monolith material medium;
partially drying the one or more whole blood samples applied to the medium such that the whole blood sample adsorbs or adheres to the porous polymer monolith material;
optionally separating any one or more regions of the medium having the one or more whole blood sample applied thereto from regions without the one or more whole blood sample applied thereto; and
optionally further drying the one or more whole blood samples applied to the one or more regions of the medium;
wherein the porous polymer monolith material medium is formed by a step-growth polymerization process, wherein the medium additionally comprises one or more supporting layers comprising a porous polymer matrix material, wherein the porous polymer matrix material of each of the one or more support layers is selected from a polyether, polyester, polycarbonate, polyanhydride, polythiophene polymer, and an epoxy resin, wherein the medium allows storage of the whole blood sample for at least one day, wherein the whole blood sample is applied directly to the medium, with the proviso that the porous polymer monolith material is polymerized onto or sits on the one or more supporting layers comprising the porous polymer matrix material without one or more intervening layers of functionality formed by photoinitiated grafting.

3. A method of analysis of a whole blood sample comprising detecting and identifying an analyte from the whole blood sample, wherein the whole blood sample was directly applied to a porous polymer monolith material medium such that the whole blood sample adsorbs or adheres to the porous polymer monolith material and stored for at least one day prior to detecting and identifying the analyte;
wherein the porous polymer monolith material medium is formed by a step-growth polymerization process, wherein the medium additionally comprises one or more supporting layers comprising a porous polymer matrix material, wherein the porous polymer matrix material of each of the one or more support layers is selected from a polyether, polyester, polycarbonate, polyanhydride, polythiophene polymer, and an epoxy resin, wherein the medium allows storage of the whole blood sample for at least one day, wherein the whole blood sample is applied directly to the medium, with the proviso that the porous polymer monolith material is polymerized onto or sits on the one or more supporting layers comprising the porous polymer matrix material without one or more intervening layers of functionality formed by photoinitiated grafting.

4. A method for storing and subsequent analysis of a whole blood sample comprising one or more analytes selected from pharmaceutical agents, peptides, proteins, oligonucleotides, DNA, RNA, oligosaccharides and lipids, the method comprising:
applying the whole blood sample comprising the one or more analytes directly to a porous polymer monolith material medium, wherein the porous polymer monolith material medium is formed by a step-growth polymerization process, wherein the medium additionally comprises one or more supporting layers comprising a porous polymer matrix material, wherein the porous polymer matrix material of each of the one or more support layers is selected from a polyether, polyester, polycarbonate, polyanhydride, polythiophene polymer, and an epoxy resin, wherein the medium allows storage of the whole blood sample for at least one day, wherein the whole blood sample is applied directly to the medium, with the proviso that the porous polymer monolith material is polymerized onto or sits on the one or more supporting layers comprising the porous polymer matrix material without one or more intervening layers of functionality formed by photoinitiated grafting;
drying the whole blood sample applied to the medium such that the whole blood sample adsorbs or adheres to the porous polymer monolith material;
storing the whole blood sample in the medium for at least one day;
retrieving and optionally pre-treating the stored whole blood sample;
and
analyzing the retrieved and optionally pre-treated whole blood sample for the presence of one or more analytes.

5. The method of claim 1 wherein the porous polymer monolith material medium has an integral body with a pore size and a specific surface area adapted to facilitate the drying and storage of the biological fluid sample, wherein the pore size of the porous polymer monolith material is in the range of 5 to 10,000 nm and the specific surface area of the porous polymer monolith material when measured by nitrogen adsorption using BET isotherm is in the range of 0.5 to 1000 $m^2/g$.

6. The method of claim 2 wherein the porous polymer monolith material medium has an integral body with a pore size and a specific surface area adapted to facilitate the drying and storage of the biological fluid sample, wherein the pore size of the porous polymer monolith material is in the range of 5 to 10,000 nm and the specific surface area of the porous polymer monolith material when measured by nitrogen adsorption using BET isotherm is in the range of 0.5 to 1000 $m^2/g$.

7. The method of claim 3 wherein the porous polymer monolith material medium has an integral body with a pore size and a specific surface area adapted to facilitate the drying and storage of the biological fluid sample, wherein the pore size of the porous polymer monolith material is in the range of 5 to 10,000 nm and the specific surface area of the porous polymer monolith material when measured by nitrogen adsorption using BET isotherm is in the range of 0.5 to 1000 $m^2/g$.

8. The method of claim 4 wherein the porous polymer monolith material medium has an integral body with a pore size and a specific surface area adapted to facilitate the drying and storage of the biological fluid sample, wherein the pore size of the porous polymer monolith material is in the range of 5 to 10,000 nm and the specific surface area of the porous polymer monolith material when measured by nitrogen adsorption using BET isotherm is in the range of 0.5 to 1000 $m^2/g$.

9. The method of claim 1 wherein the porous polymer monolith material is incorporated with chemical functionality selected from the group consisting of hydrophilic groups and groups with ion exchange properties to facilitate pre-analysis of analytes in the whole blood sample or in situ elimination of undesirable components in the whole blood sample on the medium.

10. The method of claim 2 wherein the porous polymer monolith material is incorporated with chemical functionality selected from the group consisting of hydrophilic groups and groups with ion exchange properties to facilitate pre-analysis of analytes in the whole blood sample or in situ elimination of undesirable components in the whole blood sample on the medium.

11. The method of claim 3 wherein the porous polymer monolith material is incorporated with chemical functionality selected from the group consisting of hydrophilic groups and groups with ion exchange properties to facilitate pre-analysis of analytes in the whole blood sample or in situ elimination of undesirable components in the whole blood sample on the medium.

12. The method of claim 4 wherein the porous polymer monolith material is incorporated with chemical functionality selected from the group consisting of hydrophilic groups and groups with ion exchange properties to facilitate pre-analysis of analytes in the whole blood sample or in situ elimination of undesirable components in the whole blood sample on the medium.

13. The method of claim 1 wherein the step-growth polymerization process for the porous polymer monolith material comprises the polymerization of one or more monomers having one or more functional groups selected from: hydroxyl, carboxylic acid, anhydride, acyl halide, alkyl halide, acid anhydride, acrylate, methacrylate, aldehyde, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, azide, and combinations thereof.

14. The method of claim 2 wherein the step-growth polymerization process for the porous polymer monolith material comprises the polymerization of one or more monomers having one or more functional groups selected from: hydroxyl, carboxylic acid, anhydride, acyl halide, alkyl halide, acid anhydride, acrylate, methacrylate, aldehyde, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, azide, and combinations thereof.

15. The method of claim 3 wherein the step-growth polymerization process for the porous polymer monolith material comprises the polymerization of one or more monomers having one or more functional groups selected from: hydroxyl, carboxylic acid, anhydride, acyl halide, alkyl halide, acid anhydride, acrylate, methacrylate, aldehyde, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, azide, and combinations thereof.

16. The method of claim 4 wherein the step-growth polymerization process for the porous polymer monolith material comprises the polymerization of one or more monomers having one or more functional groups selected from: hydroxyl, carboxylic acid, anhydride, acyl halide, alkyl halide, acid anhydride, acrylate, methacrylate, aldehyde, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, azide, and combinations thereof.

17. The method of claim 13, wherein the acrylic acid monomer is a methacrylate monomer.

18. The method of claim 14, wherein the acrylic acid monomer is a methacrylate monomer.

19. The method of claim 15, wherein the acrylic acid monomer is a methacrylate monomer.

20. The method of claim 16, wherein the acrylic acid monomer is a methacrylate monomer.

21. The method of claim 17 wherein the methacrylate monomer is selected from hydroxyethyl methacrylate (HEMA) and ethylene glycol dimethacrylate (EDMA).

22. The method of claim 18 wherein the methacrylate monomer is selected from hydroxyethyl methacrylate (HEMA) and ethylene glycol dimethacrylate (EDMA).

23. The method of claim 19 wherein the methacrylate monomer is selected from hydroxyethyl methacrylate (HEMA) and ethylene glycol dimethacrylate (EDMA).

24. The method of claim 20 wherein the methacrylate monomer is selected from hydroxyethyl methacrylate (HEMA) and ethylene glycol dimethacrylate (EDMA).

* * * * *